US006369241B1

(12) United States Patent
Xu et al.

(10) Patent No.: US 6,369,241 B1
(45) Date of Patent: Apr. 9, 2002

(54) METHODS FOR PREPARING ANTIVIRAL CALANOLIDE COMPOUNDS

(75) Inventors: Ze-Qi Xu, Naperville, IL (US); Hongwei Yuan, Foster City, CA (US); Jennifer Crabb, Chicago, IL (US); Raghu Samy, Schaumburg, IL (US); Ailing Li, Carol Stream, IL (US); Hua Cao, Chicago, IL (US)

(73) Assignee: Sarawak Medichem Pharmaceuticals, Inc., Lemont, IL (US)

(*) Notice: Subject to any disclaimer, the term of this patent is extended or adjusted under 35 U.S.C. 154(b) by 0 days.

(21) Appl. No.: 09/557,821

(22) Filed: Apr. 25, 2000

Related U.S. Application Data

(60) Provisional application No. 60/131,059, filed on Apr. 26, 1999.

(51) Int. Cl.⁷ ............................................ C07D 311/22
(52) U.S. Cl. ............................... 549/277; 514/453
(58) Field of Search ............................... 549/277

(56) References Cited

U.S. PATENT DOCUMENTS

| | | |
|---|---|---|
| 4,601,987 A | 7/1986 | Klibanov et al. |
| 5,010,012 A | 4/1991 | Wullbrandt et al. |
| 5,447,865 A | 9/1995 | Wong et al. |
| 5,489,697 A | 2/1996 | Boulanger et al. |
| 5,608,085 A | 3/1997 | Baker et al. |
| 5,840,921 A | 11/1998 | Flavin et al. |
| 5,843,990 A | 12/1998 | Baker et al. |
| 5,847,164 A | 12/1998 | Flavin et al. |
| 5,859,050 A | 1/1999 | Flavin et al. |
| 5,869,324 A | 2/1999 | Flavin et al. |
| 5,872,264 A | 2/1999 | Flavin et al. |
| 5,874,591 A | 2/1999 | Flavin et al. |
| 5,892,060 A | 4/1999 | Flavin et al. |

FOREIGN PATENT DOCUMENTS

| | | |
|---|---|---|
| WO | WO 92/06695 | 4/1992 |
| WO | WO 93/20082 | 10/1993 |
| WO | WO 94/14789 | 7/1994 |
| WO | WO 94/28000 | 12/1994 |
| WO | WO 95/29920 | 11/1995 |
| WO | WO 96/26934 | 9/1996 |
| WO | WO 98/38193 | 9/1998 |

OTHER PUBLICATIONS

Gustafson et al. (1992), "A Nonpromoting Phorbol from the Samoan Medicinal Plant *Homalanthus nutans* Inhibits Cell Killing by HIV–1," J. Med. Chem., vol. 35, pp. 1978–1986.
Gustafson et al. (1992), "AIDS–Antiviral Natural Products Research at the U.S. National Cancer Inst." in *Natural Products as Antiviral Agents,* Chu et al., eds. Plenum Press, New York, 1992, pp. 57–67.
Kawazu et al. (1972), "Piscicidal Constituents of *Capophyllum inophyllum,*" Chemical Abstracts, vol. 78, Abstract No. 13744F.

Kumar et al. (1982), "Calocalabaxanthone, The Putative Isoprenyl Precursor of Calabaxanthone From *Calophyllum Calaba,*" Phytochemistry, vol. 21, pp. 807–809.
Merigan et al. (1991), "Treatment of AIDS with Combinations of Antiretroviral Agents," Am. J. Medicine, vol. 90, pp. 8S–17S.
Boyd, R., "Challenges in Developing a New Drug from Tropical Rain Forest Plants," Abstract pp. 1–22.
Somanathan et al. (1974), "Chemical Investigation of Ceylonese Plants. Part VIII. Trapezifolixanthone, a New Di–isoprenylated Xanthone from the Bark of *Calophyllum trapezifolium* Thw. (Guttiferae)," J.C.S. Perkin I, pp. 2515–2517.
White et al. (1991), "A TIBO Derivative, R82913, Is A Potent Inhibitor of HIV–1 Reverse Transcriptase with Heteropolymer Templates," Antiviral Research, vol. 16, pp. 257–266.
Cragg et al. (1993), Conservation of Biodiversity and the Potential for Development of Pharmaceutical Crops: Drug Discovery and Development at the United States National Cancer Institute, In *Proceedings of the Symposium on the Industrial Utilization of Tropical Plants and the Conservation of Biodiversity,* Enugu, Nigeria, Feb. 14–19.
Hertzberg et al. (1993), "Kinetic Studies of HIV–1 Reverse Transcriptase Inhibition by Inophyllums, A Novel Class of Non–Nucleoside Inhibitors, Using a Scintillation Proximity Assay," *Programs and Abstracts of the Third International Conference on the Biotechnology of Microbial Products; Novel Pharmacological and Agrobiological Activities,* P–42, 27, Apr. 1993.
Hertzberg et al. (1993), "Novel Methods for Antiviral Drug Discovery," *Programs and Abstracts of the Third International Conference on the Biotechnology of Microbial Products; Novel* Pharmacological and Agrobiological Acitivities, S–9, 17, Apr. 1993.
Mabberley, D.J. (1987), *The Plant Book,* Cambridge University Press, p. 92.

(List continued on next page.)

Primary Examiner—Floyd D. Higel
Assistant Examiner—Donya N. Wright
(74) Attorney, Agent, or Firm—McDonnell, Boehnen Hulbert & Berghoff

(57) ABSTRACT

The present invention relates to methods for preparing 2,2-dimethyl-5-acyloxy-10-propyl-2H,8H-benzo[1,2-b:3,4-b']dipyran-8-one (5) and 2,2-dimethyl-5-hydroxy-10-propyl-2H,8H-benzo[1,2-b:3,4-b']dipyran-8-one (6) and their use as intermediates for the synthesis of antiviral calanolide compounds. For example, Fries rearrangement on compound 5 or Friedel-Crafts reaction on 6, yields intermediate 2,2-dimethyl-5-hydroxy-6-propionyl-10-propyl-2H, 8H-benzo[1,2-b:3,4-b']dipyran-8-one (4), which, in turn, can be converted to (+)-calanolide A and (−)-calanolide B. The coupling of compound 6 with the appropriate chiral molecule under Mitsunobu or nucleophilic displacement leads to the asymmetric synthesis of antiviral calanolide compounds.

8 Claims, 9 Drawing Sheets

OTHER PUBLICATIONS

Patil et al. (1993), "The Inophyllums, Novel Inhibitors of HIV–1 Reverse Transcriptase," *Programs and Abstracts of the Third International Conference on the Biotechnology of Microbial Products: Novel Pharmacological and Agrobiological Activities*, P–31, 26, Apr. 1993.

Zembower, et al., Structural Analogues of Calanolide Anti–HIV Agents. Modifications of the trans–10, 11–Dimethyldihydropyran–12–ol ring (Ring C)[1], J. Med. Chem., vol. 40, 1997, pp. 1005–1017.

Hadden, J., "TIPS Reviews: Immunotherapy of human immunodeficiency virus infection," TiPS, vol. 12, 1991, pp. 107–111.

Cooper et al. (1994), GR15987 and Related Analogues as Highly Potent, Orally Active Non–Peptide Neurokinin $NK_2$ Receptor Antagonists, *Bioorganic & Med. Chem. Lett.*, vol. 4, pp. 1951–1956.

Chemical Abstracts, vol. 125 (23), p. 279, 1996, Abstract No. 300646v.

Braun, et al., "The Global Epidemiology of HIV Infection and Aids," Annu. Rev. Microbiol., vol. 44, 1990, pp. 555–577.

Borch, et al., "The Cyanohydridoborate Anion as a Selective Reducing Agent," Journal of American Chemical Society, vol. 93 [12], 1971, pp. 2897–2904.

Buckheit, et al. "Resistance to 1–[(2–Hydroxyethoxy)methyl]–6–(phenylthio)thymine Derivatives is Generated by Mutations at Multiple Sites in the HIV–1 Reverse Transcriptase," *Virology*, vol. 210, 1995, pp. 186–193.

Buckheit, et al., "Cell–based and biochemical analysis of the anti–HIV activity of combinations of 3'–azido–3'–deoxythymidine and analogues of TIBO," Antiviral Chemistry & Chemotherapy, vol. 5[1], 1994, pp. 35–42.

Brookmeyer, "Reconstruction and Future Trends of the AIDS Epidemic in the United States," Science, vol. 253, 1991, pp. 37–42.

Bundgaard, et al., A Novel Lead for Specific Anti–HIV–1 Agents: 1–[(2–Hydroxyethoxy)methyl]–6–(phenyltio)thymine.

Castro, "Replacement of Alcoholic Hydroxyl Groups by Halogens and Other Nucleophiles Via Oxyphosphonium Intermediates," pp. 1–163.

Craig, et al, "Antiviral properties of R0–31–8959, an inhibitor of human immunodeficiency virus (HIV) proteinase," Antiviral Research, vol. 16, 1991, pp. 295–305.

Crombie, et al., "Synthesis of the Mammea Coumarins. Part I. The Coumarins of the Mammea A, B. and C Series," J. Chem. Soc. Perkin Trans., vol. 1, 1987, pp. 317–330.

Feuer, et al., "The Reduction of Oximes, Oximes Ethers, and Oxime Esters with Diborane. A Novel Synthesis of Amines," Journal of Organic Chemistry, vol. 34[6], 1969, pp. 1817–1821.

Feuer, et al., "The Reduction of Oximes with Diborane. A New Synthesis of N–Monosubstituted Hydroxylamines," The Journal of Organic Chemistry, vol. 30[9], 1965, pp. 2877–2880.

Fung, et al., "Reduction by Tributyltin Hydride of Carbonyl Compounds Adsorbed on Silica Gel: Selective Reduction of Aldehydes," J. Org. Chem., vol. 43[20], 1978, pp. 3977–3979.

Gemal, et al., "Lanthanoids in Organic Synthesis. 6. The Reduction of x–Enones by Sodium Borohydride in the Presence of Lanthanoid Chlorides: Synthetic and Mechanistic Aspects," Journal of American Chemical Society, vol. 103, 1981, pp. 5454–5459.

Gustafson, et al., "A nonpromoting Phorbol from the Samoan Medicinal Plant Homalanthus nutans Inhibits Cell Killing by HIV–1," Journal of Medicinal Chemistry, vol. 35[11], 1992, pp. 1978–1986.

Hertzberg, et al., "Novel Methods for Antiviral Drug Discovery," Third International Conference on the Biotechnology of Microbial Products, 1993, S–9 (Abstract Only).

Huff, J., "HIV Protease: A Novel Chemotherapeutic Target for AIDS," Journal of Medicinal Chemistry, vol. 34[8], 1991, pp. 2305–2314.

Hughes, D., "The Mitsunobu Reaction," Organic Reactions, vol. 42, 1992, pp. 335–657.

Khilevich, et al., "Synthesis Of (+)–Calanolide A, AN Anti–HIV Agent, Via Enzyme–Catalyzed Resolution Of The Aldol Products," Tetrahedron Asymmetry, vol. 7[11], 1996, pp. 33315–3326.

Kukla, et al., "Synthesis and Anti–HIV–1 Activity of 4,5,6, 7–Tetrahydro–5–methylimidazo[4,5,1–jk][1,4] benzodiazepin–2(1H)–one (TIBO) Derivatives," Journal of Medicinal Chemistry, vol. 34 [2], 1991, pp. 746–751.

Lin, et al., "Synthesis and Biological Evaluation of 2',3'–Dideoxy–L–pyrimidine Nucleosides as Potential Antiviral Agents against Human Immunodeficiency Virus (HIV) and Hepatitis B Virus (HBV)," Journal of Medicinal Chemistry, vol. 37[6], 1994, pp. 798–803.

McCaffrey, et al., "A Rapid Fluorometric DNA Assay for the Measurement of Cell Density and Proliferation In Vitro," In Vitro Cellular & Developmental Biology, vol. 24[3]Part I, 1988, pp. 247–252.

McGuigan, et al., "Synthesis and anti–HIV activity of some novel diaryl phosphate derivatives of AZT," Antiviral Research, vol. 24, 1994, pp. 69–77.

McMahon, et al., "Diarylsulfones, a New Chemical Class of Nonucleoside Antiviral Inhibitors of Human Immunodeficiency Virus Type 1 Reverse Transcriptase," Antimicrobial Agents and Chemotherapy, vol. 37 [4], 1993, pp. 754–760.

Massa, et al., "Synthesis and antiviral activity of new 3,4–dihydro–2–alkoxy–6–benzyl–4–oxopyrimidines (DABOs), specific inhibitors of human immunodeficiency virus type 1," Antiviral Chemistry & Chemotherapy, vol. 6[1], 1995, pp. 1–8.

Mayaux, et al., "Triterpene derivatives that block entry of human immunodeficiency virus type 1 into cells," Proc. Natl. Acad. Sci. USA, vol. 91, 1994, pp. 3564–3568.

Meier, et al., "O–Alkyl–5',5'–dinucleoside Phosphates as Prodrugs of 3'—Azidothymidine and Cordycepin[1]," J. Org. Chem., vol. 57[26], 1992, pp. 7300–7308.

Merigan, T., "Treatment of AIDS with Combinations of Antiretroviral Agents," The American Journal of Medicine, vol. 90[4A], 1991, pp. 4A–8S–4A–18S.

Brookmeyer, R. (1991), *Science*, vol. 253, pp. 37–42.

Braun et al. (1990), *Annu. Rev. Microbiol.*, vol. 44, pp. 555–577.

Weislow et al. (1989), *J. Natl. Cancer Inst.*, vol. 81, 577–586.

Mitsuya et al. (1990), *Science*, vol. 249, pp. 1533–1544.

Petteway et al. (1991), *Trends Pharmacol. Sci.*, vol. 12, pp. 28–34.

Richman, D.D. (1991), *Annu. Rev. Med.,* vol. 42, pp. 69–90.

Huff, J.R. (1991), *J. Med. Chem.,* vol. 34, pp. 2305–2314.

De Clercq, E. (1992), *AIDS Research and Human Retroviruses,* vol. 8, pp. 119–134.

Kashman et al. (1992), *J. Med. Chem.,* vol. 35, pp. 2735–2743.

Chenera et al. (1993), J. Org. Chem., vol. 58, pp. 5605–5606.

Sethna et al. (1953), Organic Reactions, Chapter 1, pp. 1–58.

Crombine et al. (1987), Chem. Soc., vol. 1, pp. 317–330.

Barton et al. (1990), *Tetrahedron Letters,* vol. 31, pp. 7449–7452.

Széll et al. (1969), Helvetica Chimica Acta, vol. 52, pp. 2636–2641.

Fung et al. (1978), *J. Org. Chem.,* vol. 43, pp. 3977–3979.

Gemal et al. (1981), J. Am. Chem. Soc., vol. 103, pp. 5454–5459.

Palmer et al. (1994), "Synthesis of the *Calophyllum coumarins,*" *Tet. Letters,* vol. 35, pp. 5363–5366.

Games et al. (1972), "Identification of 4–Phenyl and 4–Alkycoumarins in Mammea Americana L., Mammea Africana G. Don and Calophyllum Inophyllum by Gas Chromatograpy–Mass Spectrometry," Tet. Letters, vol. 31, pp. 3187–3190.

Crombie et al. (1966), "Isolation and Structure of Mammea B/BA, B/BB, B/BC and C/BB: A Group of 4–m–Propyl– and 4–n–Amyl–Coumarin Extractives of Mammea Americana L.," *Tet.* Letters, vol. 2, pp. 151–156.

Hizi et al. (1993), "Specific Inhibition of the Reverse Transcriptase of Human Immunodeficiency Virus Type 1 and the Chimeric Enzymes of Human Immunodeficiency Virus Type 1 and Type 2 by Nonnuceloside Inhibitors," Antimicrobial Agents and Chemotherapy, vol. 37, pp. 1037–1042.

Buckheit et al. (1995), "Resistance to 1–[(2–Hydroxyethoxy)methyl]–6–(phenylthio)thymine Derivatives is Generated by Mutations at Multiple Sites in the HIV–1 Reverse Transcriptase," Virology, vol. 210, pp. 186–193.

Boyer et al. (1993), "Analysis of Nonnucleoside Drug–Resistant Variants of Human Immunodeficiency Virus Type 1 Reverse Transcriptase," J. Virology, vol. 67, pp. 2412–2420.

McKee et al. (1995), "The Pseudocalanolides: Structure Revision of Calanolides C and D," Natural Products, vol. 58, pp. 916–920.

Kucherenko et al. (1995), "Novel Approach for Synthesis of (±)–Calanolide A and Its Anti–HIV Activity," Tet. Letters, vol. 36, pp. 5475–5478.

Gustafson et al. (1994), "Calanone, a Novel Coumarin From *Calophyllum teysmanni,*" *Tet.* Letters, vol. 35, pp. 5821–5824.

Kashman et al. (1993), "The Calanolides, a Novel HIV–Inhibitory Class of Coumarin Derivatives from the Tropical Rainforest Tree, *Calophyllum lanigerum,*" J. Med. Chem vol. 36, p. 1110.

Bader et al. (1991),"Oxathiin Carboxanilide, a Potent Inhibitor of Human Immunodeficiency Virus Reproduction," Proc. Natl. Acad. Sci. USA, vol. 88, pp. 6740–6744.

Borch et al. (1971), "The Cyanohydridoborate Anion as a Selective Reducing Agent," *J. Amer.* Chem. Soc., vol. 99, pp. 2897–2904.

Castro, B.R. (1983), "Replacement of Alcoholic Hydroxyl Groups by Halogens and Other Nucleophiles via Oxyphosphonium Intermediates," Org. React., vol. 29, pp. 1–162.

Feuer et al. (1965), "The Reduction of Oximes with Diborane. A New Synthesis of N–Monosubstituted Hydroxylamines," J. Org. Chem. vol. 30, pp. 2877–2880.

Feuer and Braunstein (1969), "The Reduction of Oximes, Oxime Ethers and Oxime Esters with Diborane. A Novel Synthesis of Amines," J. Org. Chem., vol. 34, pp. 1817–1821.

Hudlicky, M. (1988), "Fluorination with Diethylaminosulfur Trifluoride and Related Aminofluorosulfuranes," Org. React., vol. 35, pp. 513–637.

Hughes, D.L. (1992), "The Mitsunobu Reaction," *Organic Reaction,* vol. 42, pp. 335–656.

Merluzzi et al. (1990), "Inhibition of HIV–1 Replication by a Nucleoside Reverse Transcriptase Inhibitor," Science, vol. 250, pp. 1411–1413.

Mitsunobu, O. (1981), "The Use of Diethyl Azodicarboxylate and Triphenylphosphine in Synthesis and Transformation of Natural Products," Synthesis, pp. 1–28.

Miyasaka et al. (1989), "A Novel Lead for Specific Anti–HIV–1 Agents: 1–[(2–Hydroxyethoxy)methyl]–6–(phenylthio)–thymine," *J. Medicinal Chemistry,* vol. 32, pp. 2507–2509.

Nielsen and Houlihan (1968), "The Aldol Condensation," *Org. React.,* vol. 16, pp. 1–438.

Pauwels et al. (1990), "Potent and Selective Inhibition of HIV–1 Replication In Vitro by a Novel Series of TIBO Derivatives," Nature, vol. 343, pp. 470–474.

Pauwels et al. (1988), "Rapid and Automated Tetrazolium–Based Colormetric Assay for the Detection of Anti–HIV Compounds," J. Virological Methods, vol. 309–321.

Sergheraert et al. (1993), Synthesis and Anti–HIV Evaluation of D4T and D4T 5'–Monophosphate Prodrugs, J. Medicinal Chemistry, vol. 36, pp. 826–830.

Wasserman et al. (1989), "The Chemistry of Vicinal Tricarbonyls, Use of Vinyl Tricarbonyl Esters in the Formation of 3–Hydroxypyrrole–2–Carboxylates," *Tet. Letters,* vol. 30, pp. 1721–1724.

Bandara et al. (1986), "Two Chemically Distinct Groups of Calophyllum Species From Sri Lanka," Phytochemistry, vol. 25, pp. 425–428.

Buckheit, Jr., et al., Antiviral Research, vol. 26, pp. 117–132 (1995).

Boyd, M., "AIDS: Etiology, Diagnosis Treatment and Prevention," Chapter 18, 2nd Ed., J.B. Lippincott Co., Devita et al., ed., pp. 305–317.

Chaturvedi et al. (1974), "Anticonvulsant and Antinflammatory Activity of Natural Plant Coumarins and Triterpenoids," *Res. Communications in Chemical Pathology and Pharmacology,* vol. 9, pp. 11–22.

Craig et al. (1991), "Antiviral Properties of Ro 31–8959, An Inhibitor Human Immunodeficiency Virus (HIV) Proteinase," Antiviral Research, vol. 16, pp. 295–305.

Dahanayake et al. (1974), "Chemical Investigation of Ceylonese Plants. Part VII. Extractives of *Calophyllum thwaitesii* Planch and Triana and *Calophyllum walkeri* Wight (Guttiferae)," *J.C.S.* Perkin I, pp. 2510–2514.

Dharmaratne et al. (1985), "Triterpenoids and Coumarins from the Leaves of *Calophyllum Cordato–Oblongum,*" Phytochemistry, vol. 24, pp. 1553–1556.

Dharmaratne et al. (1986), "Xanthones from Roots of Three Calophyllum Species,"Phytochemistry, vol. 25, pp. 1957–1959.

Gunasekera et al. (1977), "Chemical Investigation of Ceylonese Plants. Part 27. Extractives of *Calophyllum cuneifolium Thw.* and *Calophyllum soulattri* Burm. F. (Guttiferae)," *J.C.S. Perkin I*, pp. 1505–1511.

Gunasekera et al. (1975), "Chemical Investigation of Ceylonese Plants. Part XVI. Extractives of *Calophyllum cardato–oblongum* Thw. (Guttiferae)," J.C.S. Perkin I, pp. 2215–2220.

Gunatilaka et al. (1984), "Terpenoid and Biflavanoid Constituents of *Calophyllum Calaba* and *Garcinia Spicata* From Sri Lanka," Phytochemistry, vol. 23, pp. 323–328.

Ohtani, et al. (1991), "A New Aspect of the High–Field of NMR Application of Mosher's Method. The Absolute Confirugation of Marine Triterpene Sipholenol–A," *J. Org. Chem.*, vol. 56, pp. 1296–1298.

Ohtani et al. (1989), "Absolute Configuration of Marine Diterpenes Possessing a Xenicane Skelton. An Application of an Advanced Mosher's Method," *Tetrahedron Letters*, vol. 30, pp. 3147–3150.

Rink et al. (1982), "Cytoplasmic pH and Free $Mg^{2+}$ in Lymphocytes" *J. of Cell Biology*, vol. 95, pp. 189–196.

Samaraweera et al. (1981), "Calozeylanic Acid, A New Bark Acid From Three *Calophyllum Species,*" Tetrahedron Letters, vol. 22, pp. 5083–5086.

Saunders et al. (1992), "Non–nucleoside Inhibitors of HIV Reverse Transcriptase," *Drug Design* and Discovery, vol. 8, pp. 255–263.

Shih et al. (1991), "Chimeric Human Immunodeficiency Virus Type 1/Type 2 Reverse Transcriptases Display Reversed Sensitivity to Nonnucleoside Analog Inhibitors," *Proc. Natl.* Acad. Sci. USA, vol. 88, pp. 9878–9882.

Stout et al. (1968), "Calophylum Products III. The Structures of Blancoic Acids," *J. Organic* Chemistry, vol. 33, pp. 4185–4190.

Stout et al. (1964), "The Structure of Costaloide," *J. Organic Chemistry,* vol. 29, pp. 3604–3609.

Swagler et al. (1991), "Pharmacokinetics of Anti–HIV Nucleosides in Microswine," *J. Pharm.* Pharmacol., vol. 43, pp. 823–826.

Crombie et al. (1985), Synthesis of Mammeins and Surangin A, *Tet. Letters,* vol. 26, pp. 2929–2932.

Khilevich, et al., "A versatile approach for synthesis of 2,3–dimethylochroman–4–ones, intermediate for calanolide anti–HIV agents, via aldol/Mitsunobu reactions," Chemical Abstracts: 26–Biomolecules and Their Synthetic Analogs, vol. 125 [21], 1996, Abstract No. 275454w, pp. 1216.

Palmer, et al., "Synthesis of the *Calophyllum coumarins.* Part $2^1$," J. Chem. Soc. Perkin Trans., vol. 1, 1995, pp. 3135–3152.

Galinis, et al., "Structure–Activity Modifications of the HIV–1 Inhibitors (+)–Calanolide A and (–)–Calanolide $B^1$," Md. Chem., vol. 39, 1996, pp. 4507–4510.

METHODS FOR PREPARING ANTIVIRAL CALANOLIDE COMPOUNDS

CROSS-REFERENCE

This application claims the benefit of prior U.S. provisional application Ser. No. 60/131,059, filed Apr. 26, 1999.

FIELD OF THE INVENTION

This invention relates to methods for preparing calanolides and calanolide analogues.

BACKGROUND OF THE INVENTION

Viruses, an important etiologic agent in infectious disease in humans and other mammals, are a diverse group of infectious agents that differ greatly in size, shape, chemical composition, host range, and effects on hosts. After several decades of study, only a limited number of antiviral agents are available for the treatment and/or prevention of diseases caused by viruses such as HIV, hepatitis B, herpes simplex type 1 and 2, cytomegalovirus, varicella zoster virus, Epstein Barr virus, influenza A and B, parainfluenza, adenovirus, measles, and respiratory syncytial virus. Because of their toxic effects on a host, many antiviral agents are limited to topical applications. Accordingly, there is a need for safe and effective antiviral agents with a wide-spectrum of anti-viral activity with reduced toxicity to the host.

A. Human Immunodeficiency Virus (HIV)

Human immunodeficiency virus (HIV), which was also called human T-lymphotropic virus type III (HTLV-III), lymphadenopathy-associated virus (LAV) or AIDS-associated retrovirus (ARV), was first isolated in 1982 and has been identified as the etiologic agent of the acquired immunodeficiency syndrome (AIDS) and related diseases. Since then, chemotherapy of AIDS has been one of the most challenging scientific endeavors. So far, fourteen drugs have been approved by FDA and are being clinically used as drugs for the treatment of AIDS and AIDS-related complex. Although these FDA-approved drugs can extend the life of AIDS patients and improve their quality of life, none of these drugs are capable of curing the disease. Side effects as well as the emergence of drug-resistant viral strains limit the long-term use of these agents.[1] On the other hand, the number of AIDS patients worldwide has increased dramatically within the past decade and estimates of the reported cases in the very near future also continue to rise dramatically. It is therefore apparent that there is a great need for other promising drugs having improved selectivity and activity to combat AIDS.[1] Several approaches including chemical synthesis, natural products screening, and biotechnology have been utilized to identify compounds targeting different stages of HIV replication for therapeutic intervention.[2]

The natural product screening program at the National Cancer Institute has discovered a class of remarkably effective anti-HIV compounds, named calanolides, from the rain forest tree *Calophyllum lanigerum*, with (+)-calanolide A, 1, being the most potent compound in the reported series.[3] For example, (+)-calanolide A demonstrated 100% protection against the cytopathic effects of HIV-1, one of two distinct types of HIV, down to a concentration of 0.1 μM. This agent also halted HIV-1 replication in human T-lymphoblastic cells (CEM-SS)($EC_{50}$=0.1 μM/$IC_{50}$=20 μM).[3] More interestingly and importantly, (+)-calanolide A was found to be active against both the AZT-resistant G-9106 strain of HIV as well as the pyridinone-resistant A17 virus.[3] Thus, the calanolides, classified

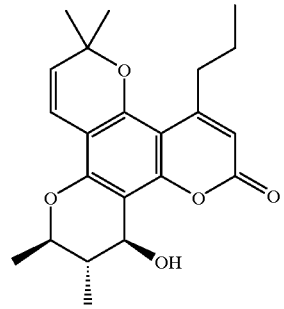

1 as HIV-1 specific reverse transcriptase inhibitors, represent novel anti-HIV chemotherapeutic agents for drug development.

B. Hepatitis B Virus (HBV)

The hepatitis B virus (HBV) infects people of all ages. It is one of the fastest-spreading sexually transmitted diseases, and also can be transmitted by sharing needles or by behavior in which a person's mucus membranes are exposed to an infected person's blood, semen, vaginal secretions, or saliva. While the initial sickness is rarely fatal, ten percent of the people who contract hepatitis are infected for life and run a high risk of developing serious, long-term liver diseases, such as cirrhosis of the liver and liver cancer, which can cause serious complications or death.[4] The World Health Organization lists HBV as the ninth leading cause of death. It is estimated that about 300 million persons are chronically infected with HBV worldwide, with over 1 million of those in the United States. The Center for Disease Control and Prevention estimates that over 300,000 new cases of acute HBV infection occurs in the United States each year, resulting in 4,000 deaths due to cirrhosis and 1,000 due to hepatocellular carcinoma.[5] The highest rates of HBV infections occur in Southeast Asia, South Pacific Islands, Sub-Saharan Africa, Alaska, Amazon, Bahai, Haiti, and the Dominican Republic, where approximately 20% of the population is chronically infected.[6]

Hepatitis B virus (HBV) infection is currently the most important chronic virus infection, but no safe and effective therapy is available at present. The major therapeutic option for carriers of HBV is alpha interferon, which can control active virus replication. However, even in the most successful studies, the response rate in carefully selected patient groups has rarely exceeded 40%.[7,8] One of the reasons cited for interferon failure is the persistence of viral supercoiled DNA in the liver.[9] Clinical exploration of many promising antiviral agents such as nucleoside analogues is hampered because their aspecific body distribution leads to significant toxic side effects. Recently, a new nucleoside analogue, 2',3'-dideoxy-3'-thiacytidine (3TC), was approved to treat HBV infection with only minimal side effects.[10-12]

C. Influenza Virus

Influenza is a viral infection marked by fever, chills, and a generalized feeling of weakness and pain in the muscle, together with varying signs of soreness in the respiratory tract, head, and abdomen. Influenza is caused by several types of myxoviruses, categorized as groups A, B, and $C_4$. These influenza viruses generally lead to similar symptoms but are completely unrelated antigenically, so that infection with one type confers no immunity against the other. Influenza tends to occur in wavelike epidemics throughout the world; influenza A tends to appear in cycles of two to three years and influenza B in cycles of four to five years. Influenza is one of the few common infectious diseases that are poorly controlled by modem medicine. Its annual epidemics are occasionally punctuated by devastating pandemics. For example, the influenza pandemic of 1918, which killed over 20 million people and affected perhaps 100 times that number, was the most lethal plague ever recorded. Since that time, there have been two other pandemics of lesser severity, the so-called Asian flu of 1957 and the Hong Kong flu of 1968. All of these pandemics were characterized by the appearance of a new strain of influenza virus to which the human population had little resistance and against which previously existing influenza virus vaccines were ineffective. Moreover, between pandemics, influenza virus undergoes a gradual antigenic variation that degrades the level of immunological resistance against renewed infection.[13]

Anti-influenza vaccines, containing killed strains of types A and B virus currently in circulation, are available, but have only a 60 to 70% success rate in preventing infection. The standard influenza vaccine has to be redesigned each year to counter new variants of the virus. In addition, any immunity provided is short-lived. The only drugs currently effective in the prevention and treatment of influenza are amantadine hydrochloride and rimantadine hydrochloride.[14-16] While the clinical use of amantadine has been limited by the excess rate of CNS side effects, rimantadine is more active against influenza A both in animals and human beings, with fewer side effects.[17,18] It is the drug of choice for the chemoprophylaxis of influenza A.[13, 19, 20] However, the clinical usefulness of both drugs is limited by their effectiveness against only influenza A viruses, by the uncertain therapeutic efficacy in severe influenza, and by the recent findings of recovery of drug-resistant strains in some treated patients.[21-25] Ribavirin has been reported to be therapeutically active, but it remains in the investigational stage of development.[26,27]

D. Cytomegalovirus (CMV)

Cytomegalovirus (CMV) is a member of the herpes virus family, other well-known members of which include herpes simplex virus, types I and II, Epstein Barr virus and Varicella Zoster virus. Although these viruses are related taxonomically, all comprising double-stranded DNA viruses, infections due to these viruses manifest in clinically distinct ways. In the case of CMV, medical conditions arising from congenital infection include jaundice, respiratory distress and convulsive seizures that may result in mental retardation, neurologic disability or death. Infection in adults is frequently asymptomatic, but may manifest as mononucleosis, hepatitis, pneumonitis or retinitis, particularly in immunocompromised patients such as AIDS sufferers, chemotherapy patients and organ transplant patients undergoing tissue rejection therapy.

Up to 45% of all HIV-infected persons will develop cytomegalovirus-induced disease before their lives end.[28] Although two antiviral agents—ganciclovir and foscarnet—are available to treat human cytomegalovirus (HCMV), they act as virustatic agents to slow but not halt progression of disease; hence, disease routinely progresses despite daily maintenance with either agent. Moreover, therapy using either agent is problematic because both agents are associated with serious toxicities.[29]

Classical drug therapies have generally focused upon interactions with proteins in efforts to modulate their disease-causing or disease-potentiating fuictions. Such therapeutic approaches have failed for cytomegalovirus infections. Effective therapy for CMV has not yet been developed despite studies on a number of antiviral agents. Interferon, transfer factor, adenine arabinoside (Ara-A), acycloguanosine (Acyclovir) and certain combinations of these drugs have been ineffective in controlling CMV infections. Based on preclinical and clinical data, foscarnet and ganciclovir show limited potential as antiviral agents. Foscarnet treatment has resulted in the resolution of CMV retinitis in five AIDS patients to date. Ganciclovir studies have shown efficacy against CMV retinitis and colitis. However, though ganciclovir seems to be well tolerated by most treated individuals, the appearance of a reversible neutropenia, the emergence of resistant strains of CMV upon long-term administration, and the lack of efficacy against CMV pneumonitis limit the long term applications of this compound. Cidofovir was approved to treat CMV in certain AIDS patients due to its undesired toxicities. The development of more effective and less toxic therapeutic compounds and methods is needed for both acute and chronic use.

Several HCMV vaccines have been developed or are in the process of development. Vaccines based on live attenuated strains of HCMV have been described. A proposed HCMV vaccine using a recombinant vaccinia virus expressing HCMV glycoprotein B has also been described. However, vaccinia models for vaccine delivery are believed to cause local reactions. Additionally, vaccinia vaccines are considered possible causes of encephalitis.

E. Other Herpes Viruses

Varicella zoster virus (VZV) is the etiologic agent that produces both varicella (chickenpox) and zoster (shingles). As with other herpes viruses, VZV causes both an acute illness and lifelong latent infection. Acute primary infection (varicella) typically occurs during childhood, where the resulting infection is relatively mild. Conversely, primary infection in adults can be more severe. Herpes zoster cutaneous eruptions are caused by reactivation of VZV present in sensory ganglia.[30] Herpes zoster occurs more frequently with elderly and immunosuppressed individuals, and is eight times more likely to develop in HIV-infected individuals than in other individuals in comparable age groups.[31]

Along with other immunosuppressed patients, HIV-infected patients may develop severe and in certain cases life-threatening illnesses following either primary or recurrent VZV infection. Therapy for HIV-infected patients experiencing VZV infection generally involves administering acyclovir or vidarabine (Ara-A), with hospitalization required in many instances. To inhibit VZV replication, serum levels of acyclovir are about ten times greater than those needed to inhibit Herpes Simplex Type 1 and 2.

Herpes simplex virus type 1 and type 2 (HSV-1 and HSV-2) can establish latency following primary infection and can thus subsequently reactivate to induce recurrent disease. Upon primary infection, herpes simplex type 1 induces diseases including primary gingivostomatitis, encephalitis, and kerato-conjunctivitis, while herpes simplex type 2 induces primary genital herpes and neonatal herpes. Upon recurrence, herpes simplex type 1 induces diseases including recurrent oral herpes and recurrent kerato-conjunctivitis, while herpes simplex type 2 induces recurrent genital herpes.[32] HSV infection in HIV-infected patients can produce widespread and occasionally life-threatening lesions.

Acyclovir, delivered either intravenously, orally, or topically, shortens clinical illness in both immunocompetent and immunosuppressed patients. Vidarabine also has been used in treating HSV. Some vaccine strategies have been investigated with a view towards preventing initial primary infection. However, protecting only against primary disease but not protecting against latency and subsequent recurrence is inadequate for those persons already initially infected. Moreover, acyclovir-resistant HSV infections recently have been observed, in many cases occurring among HIV-infected patients treated successfully with acyclovir in the past. The existence of such acyclovir-resistant infections in HIV-infected patients is troubling in view of the limited number of alternative therapeutic options available.

Respiratory Syncytial Virus (RSV) is the prime etiologic agent producing lower respiratory tract disease. RSV causes extensive yearly epidemics during which there is a marked increase in hospital admissions of patients, especially infants and young children, experiencing severe lower respiratory tract disease. Immunosuppressed patients infected with RSV are at high risk of mortality. Ribavirin is the only currently approved drug for treating RSV infections. However, this drug appears to have limited efficacy. Additionally, development of effective vaccines has proven difficult to date.

F. Opportunistic Infections

The viruses described above can act as sole causes of infection or can act to produce opportunistic infections in patients already battling inununosuppressing infections such as HIV. Acting by themselves, these viruses can present therapeutic challenges. But when acting to produce opportunistic infections in HIV-infected or other immunosuppressed patients, these viruses dramatically increase the difficulty and complexity of successful treatment.

In addition to the viruses discussed above, other viral, bacterial, fungal, and protozoal pathogens can induce opportunistic infections. Common opportunistic pathogens in addition to those described above include *Mycobacterium avium* complex (MAC), *Pneumocystis carinii* (PC), and *M. tuberculosis*.

Present therapies for HIV-infected patients also suffering from opportunistic infection generally involve administering a plurality of antiviral compounds. In such a treatment regimen, termed combination therapy, each antiviral compound employed demonstrates best antiviral activity against a distinct viral infection. For example, a combination therapy of AZT and ganciclovir can be used for an HIV-infected patient also experiencing CMV retinitis, where AZT targets the HIV infection and ganciclovir targets the CMV infection. Thus, combination therapies can be powerful therapeutic tools. Even more powerful and desirable, however, would be a single antiviral compound that demonstrates antiviral activity against both HIV and other viruses.

While some limited success has been realized in the search for viable therapeutics for treatment of the viral infections discussed above, therapeutic agents for many viruses remain severely limited. Furthermore, there are no known safe and therapeutic treatments for HBV, influenza and HIV. In HBV, with the possible exception of the drug 3TC, the use of nucleoside-based antiviral agents leads to toxicity, probably due to cross-inhibition of cellular mitchondrial DNA. Clearly, there is a need for a new class of antiviral agents which could minimize the toxicity associated with cross-inhibition. In influenza, amantadine and rimantadine have been shown to be moderately effective against only influenza A viruses, with amantadine having excessive side effects. Recently, strains of influenza A resistant to amantadine and rimantadine have been isolated. Accordingly, there is a need for new types of therapeutic antiviral agents particularly against both influenza A and influenza B, as well as against HIV, HBV and HIV and other viruses. Furthermore, due to the loss of CD4 T lymphocytes in an HIV infected person, leading to immunodeficiency and thus increasing susceptibility to a broad range of opportunistic viral, bacterial, fungal, and protozoal pathogens, identifing anti-HIV agents having a spectrum of antiviral and antimicrobial activities is of particular interest. These agents would be not only effective against HIV infection, but also effective against or preventive of opportunistic infections in AIDS patients.

A class of coumarin compounds, either natural products isolated from several tropical plants of the genus Calophyllum[3, 33-38] or synthetic analogues,[39-41] have been demonstrated to be active against HIV-1. (+)-Calanolide A (1), the most active one in this class, has been selected for further pharmacological and clinical development.[42,43] However, a natural source of (+)calanolide A is limited. This limited availability fueled the desire to develop practical synthesis routes to enable further study and development to be carried out on this active and promising series of compounds. Herein, we describe improved synthetic approaches for the synthesis of important intermediates for the synthesis of antiviral calanolide compounds.

SUMMARY OF THE INVENTION

The present invention relates to synthetic approaches for preparing antiviral calanolides and key intermediates thereof. A number of total syntheses of calanolide compounds have been reported by us[44-46] and by others.[47-51] In our previous syntheses (FIG. 1),[44-46] 2,2-dimethyl-5-hydroxy-6-propionyl-10-propyl-2H,8H-benzo[1,2-b:3,4-b'] dipyran-8-one (4) was the key intermediate, which was derived from 5,7-dihydroxy-8-propionyl-4-propylcoumarin (3). In this application, we report a novel approach to the synthesis of 2,2-dimethyl-5-acyloxy-10-propyl-2H,8H-benzo[1,2-b:3,4-b']dipyran-8-one (5) and 2,2-dimethyl-5-hydroxy-10-propyl-2H,8H-benzo[1,2-b:3,4-b']dipyran-8-one (6) (FIGS. 3 and 4). These compounds serve as important intermediates for the synthesis of antiviral calanolide compounds. For example, Fries rearrangement[52-54] on compound 5a, or Friedel-Crafts reaction on 6, yields intermediate 4, which, in turn, can be converted to (+)-calanolide A and (−)-calanolide B[44-46] (FIGS. 1 and 5).

Thus, in one embodiment of the invention, a method for preparing (+)-calanolide A using 6 is provided. According to the method, 6 is coupled to compound 11 to provide compound 13. Compound 13 is subsequently hydrolyzed to produce 13 (Y=OH). Compound 13 (Y=OH) is then subjected to an intramolecular Friedel-Crafts reaction to provide ketone (+)-10. Ketone (+)-10 is then subjected to Luche reduction to produce (+)-calanolide A 1 (FIG. 6).

Alternatively, compound 13 may be prepared from compound 6 by treating the latter compound with 12 to produce 14. Compound 14 is then subject to a Swern oxidation to produce aldehyde 13 (Y=H). Compound 13 (Y=H) is subsequently oxidized to provide 13 (Y=OH) (FIG. 7).

In another embodiment of the invention, a general method for providing calanolide analogues is provided. According to this method, 1,3,5-triphenol is reacted with β-keto 25 ester under Peckmnan conditions.[44-46] The resulting compound 15 is then selectively acylated to provide compound 16. Compound 16 is then chromenylated to produce compound 17.[44-46] Hydrolysis of 17 produced compound 18 which is then coupled with ester 19 to produce 20. Compound 20 was then cyclized under Friedel-Crafts conditions to produce 21. Reduction of 21 with a suitable reagent, e.g. sodium borohydride, results in calanolide analogue 22 (FIG. 8).[44-46]

Alternatively, compound 20 may be prepared from compound 18 by coupling the latter compound with 23 to produce 24. Compound 24 was then subject to swern oxidation to produce the aldehyde analogue 20 (Y=H). The aldehyde analogue was then oxidized to produce the carboxylic analogue 20 (Y=OH) (FIG. 9).

These and other embodiments of the invention will become apparent in light of the detailed description below.

DETAILED DESCRIPTION OF THE FIGURES

FIG. 2 is a retrosynthetic schematic illustrating the conversion of intermediates 2to7to5a.

Figure 3:
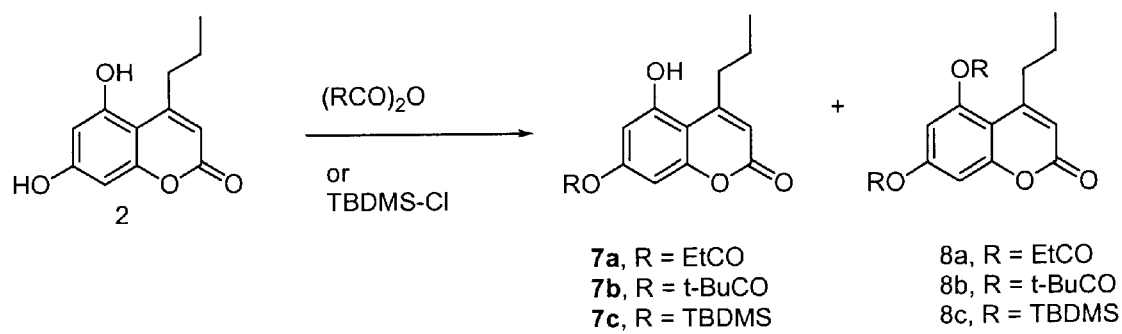

FIG. 3 illustrates selective acylation reactions of coumarin 2 to form compounds 7a–c and 8a–c.

Figure 4:
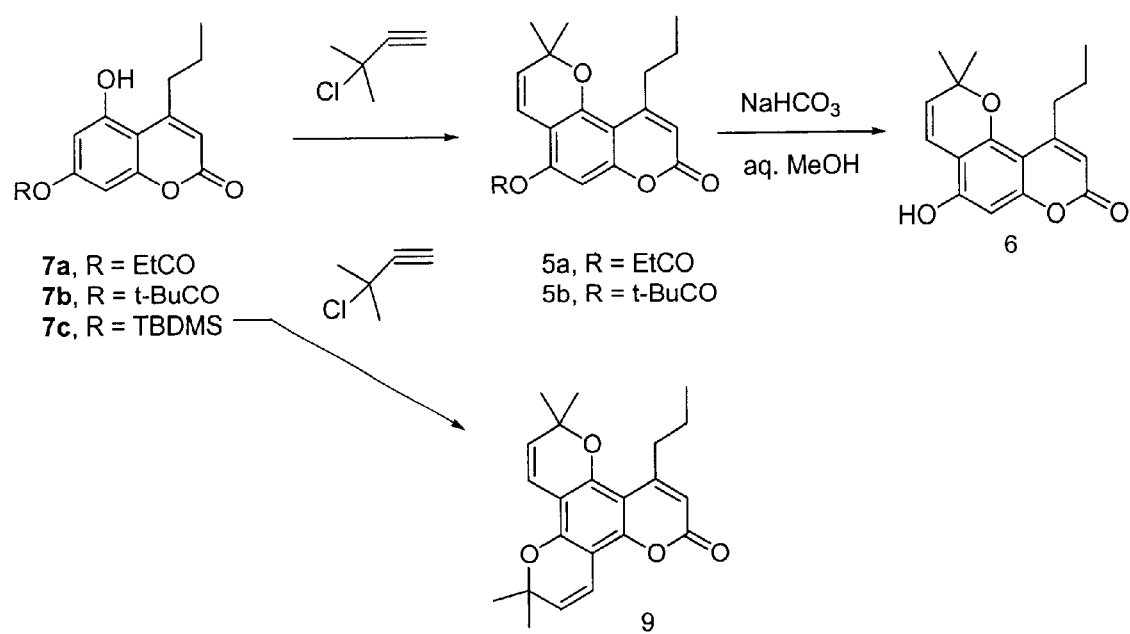

FIG. 4 illustrates the chromenylation of coumarin compounds 7a–c to 5a–b and the basic hydrolysis of acylated chromeno-coumarin 5a–b to compound 6.

Figure 5:
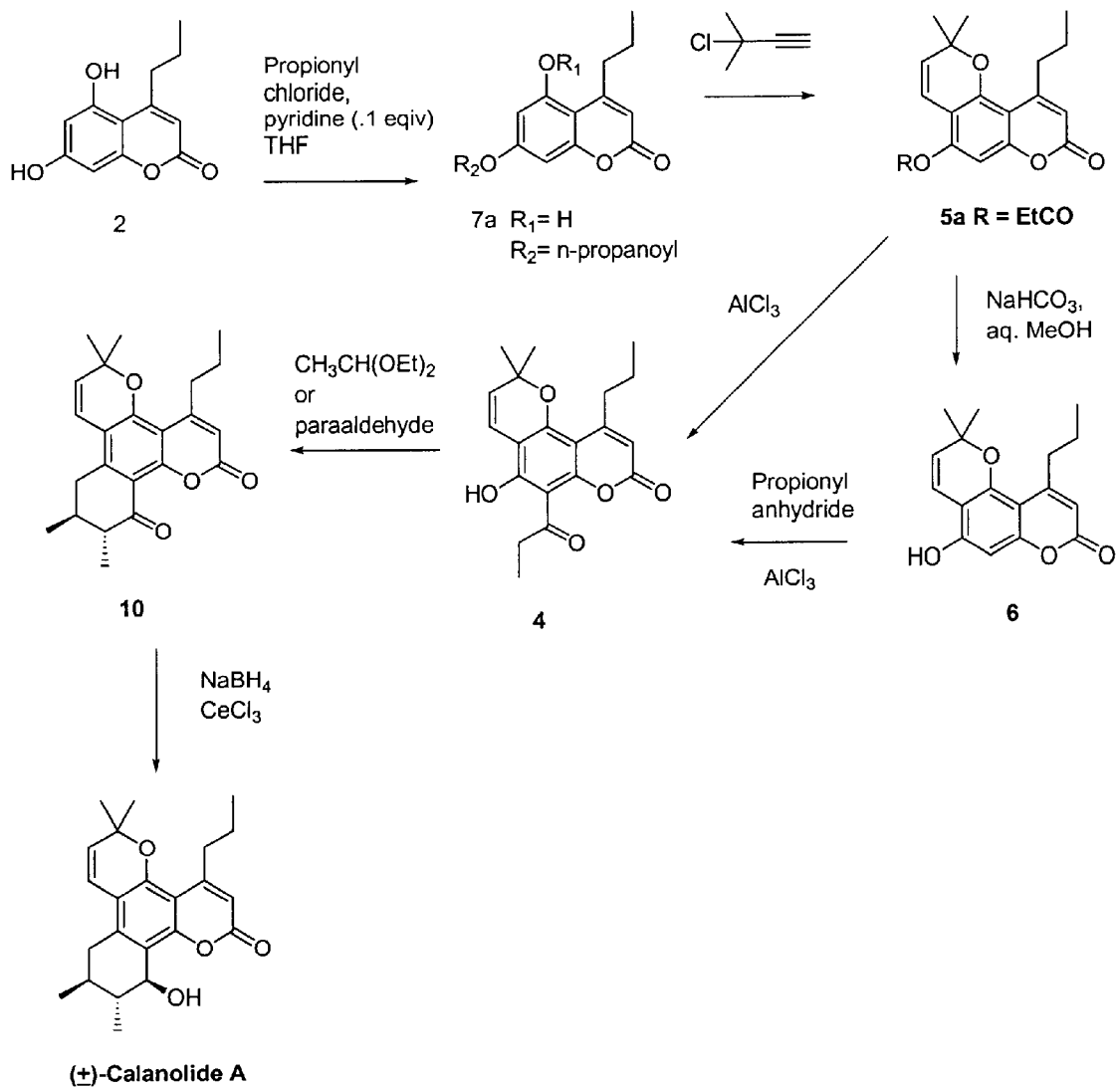

FIG. 5 illustrates the conversion of key intermediates 5a and 6 to (±)-calanolide A.

Figure 6:
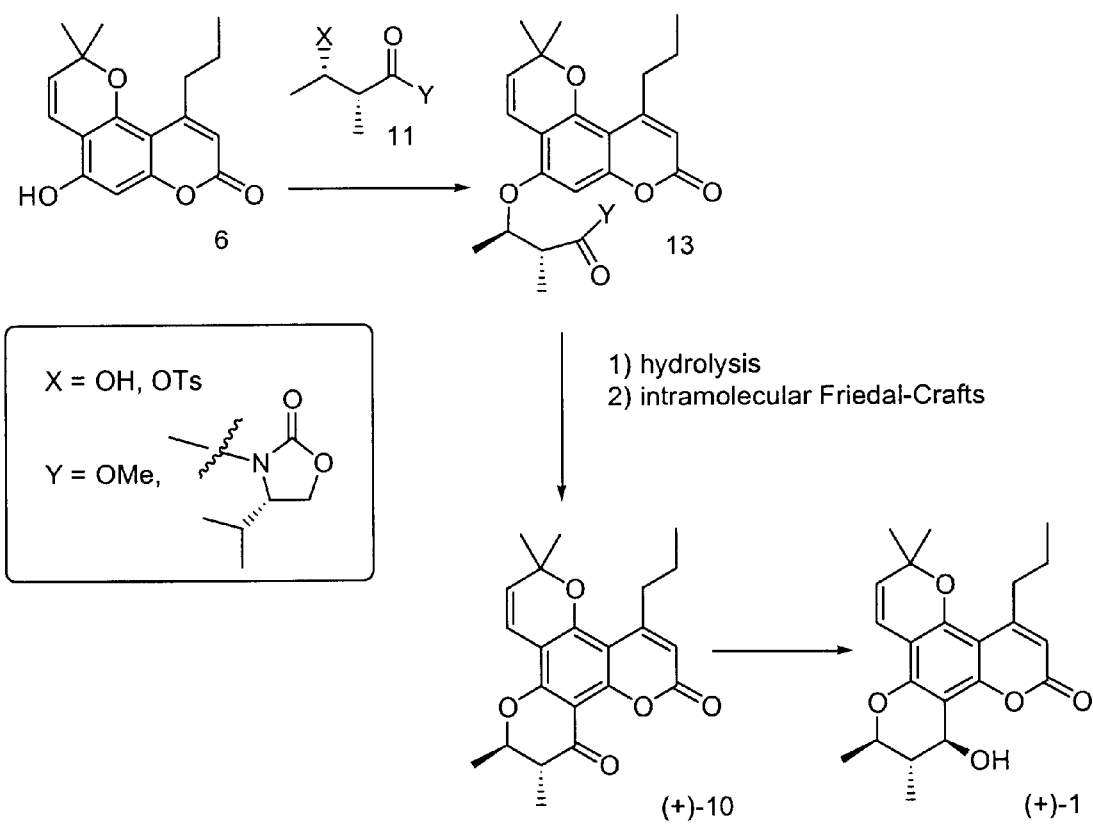
Figure 7:
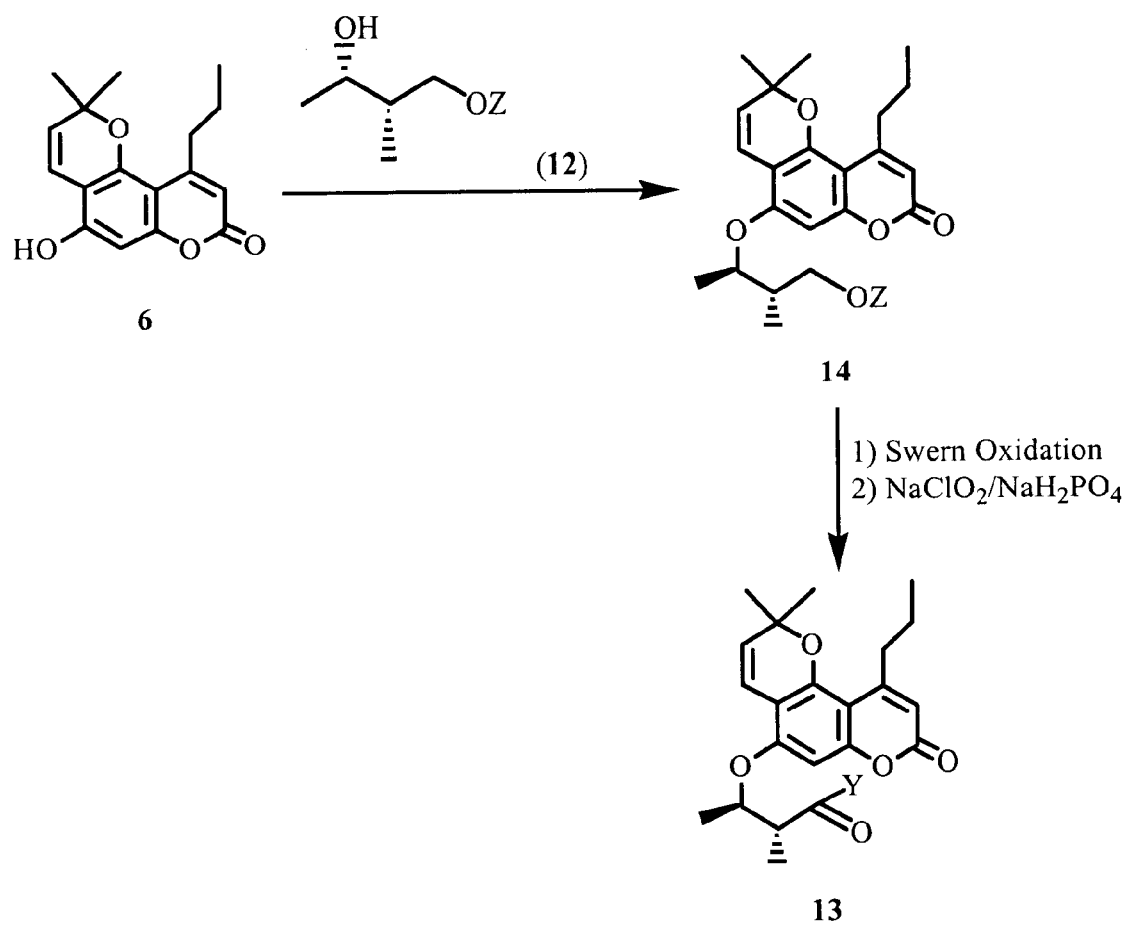

FIGS. 6 and 7 further illustrate preparation of (+)-calanolide A from 6.

Figure 8:
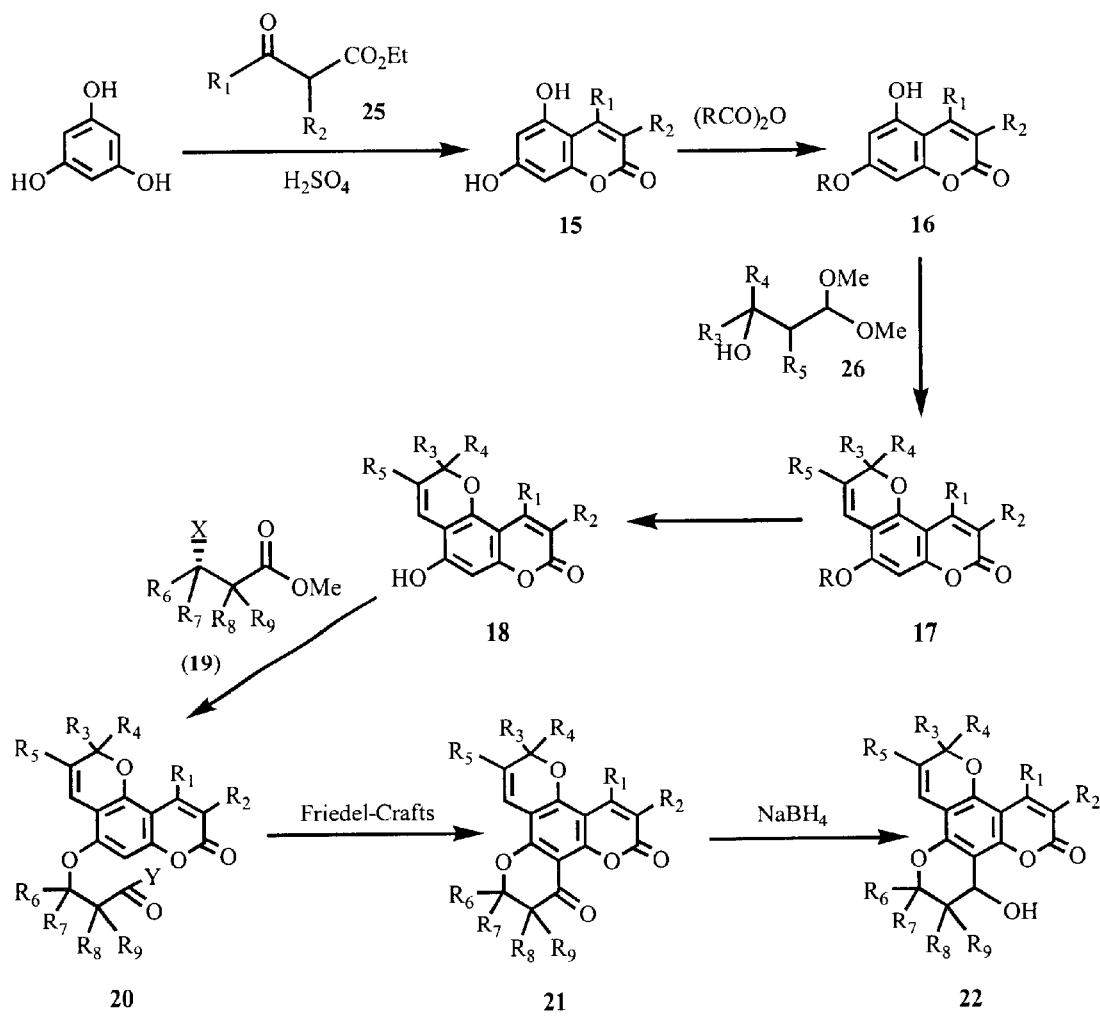
Figure 9:
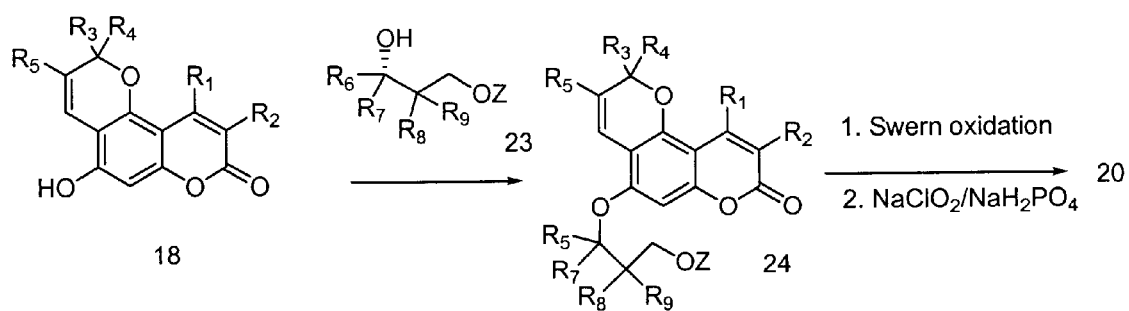

FIGS. 8 and 9 illustrate preparation of calanolide analogues.

DETAILED DESCRIPTION OF THE INVENTION

Figure 1:
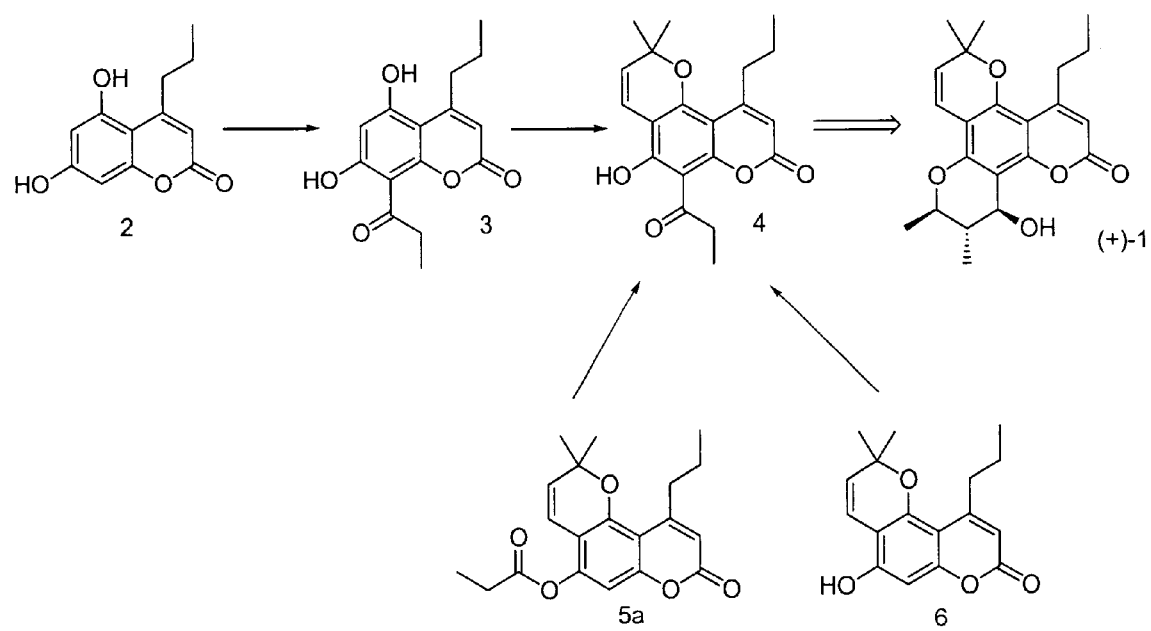
FIG. 1 is a schematic illustrating the conversion of compounds 5(a) and 6 to 4, a key intermediate for the preparation of calanolides such as (+)-calanolide A.

The present invention relates to methods for preparing (+)-calanolide A and calanolide analogues. In one embodiment of the invention, a novel approach to the synthesis of 2,2-dimethyl-5-acyloxy-10-propyl-2H,8H-benzo[1,2-b:3,4-b']dipyran-8-one (5) and 2,2-dimethyl-5-hydroxy-10-propyl-2H,8H-benzo[1,2-b:3,4-b']dipyran-8-one (6) is provided. These compounds serve as important intermediates for the synthesis of antiviral calanolide compounds. For example, Fries rearrangement[52-54] on compound 5a, or Friedel-Crafts reaction on 6, yields intermediate 4, which, in turn, can be converted to (+)-calanolide A and (−)-calanolide B[44-46] (FIGS. 1 and 5).

Figure 2:
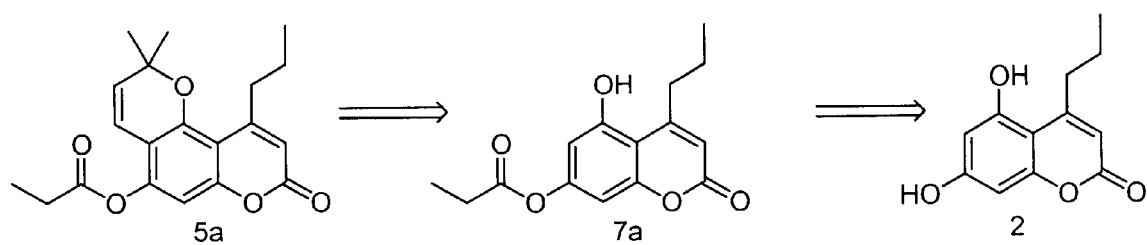

The strategy for synthesis of compound 5a is based on the fact that under the modified Friedel-Crafts reaction conditions 5-hydroxy-7-propionyloxy-4-propylcoumarin (7a) was selectively formed from 2 in 10% yield. Chromenylation[44,45] on 7a is expected to deliver compound 5a (FIG. 2). Due to the low yields from the Friedel-Crafts acylation reaction, a more practical procedure needed to be developed for the synthesis of 7a from 2. A variety of reaction conditions were investigated, which is summarized in Table I in Example 1. Accordingly, improved acylation conditions were discovered which provided surprisingly increased production yields of 7a.

In conducting this reaction, a solution of suitable acylating agent, e.g., acyl chloride or anhydride, in a suitable solvent, e.g., THF, was added in a dropwise manner to a vigorously stirred solution of 5,7-dihydroxy-4-propylcoumarin 2, a Lewis acid catalyst or a catalytic amount of a base, and an organic solvent cooled in an ice bath. Dropwise addition of the acylating agent is conducted such that the temperature of the reaction mixture is maintained at a temperature ranging between 0° C. and about 30° C.

In making compounds of the invention, the amount of acylating agent used generally ranges between about 0.5 and about 6 moles, preferably ranging between about 1 and about 2 moles, per mole of 2.

Non-limiting examples of Lewis acid catalysts useful in the acylation reaction include $AlCl_3$, $BF_3$, $SnCl_4$, $ZnCl_2$, $POCl_3$ and $TiCl_4$. A preferred Lewis acid catalyst is $AlCl_3$. The amount of Lewis acid catalyst relative to 5,7-dihydroxy-4-propylcoumarin, 2, ranges between about 0.5 and about 12 moles, preferably ranging between about 2 and about 5 moles, per mole of 5,7-dihydroxy-4-propylcoumarin, 2.

Non-limiting examples of a base useful in the acylation reaction include pyridine and 4-dimethylaminopyridine (DMAP). Catalytic amounts (0.1 eq) of the base may be used in combination with a suitable reaction solvent. Alternatively, the base may be used as the reaction solvent, however, complex product mixtures may results (Example 1).

Non-limiting examples of organic solvent for use in the acylation reaction include THF, dichloroethane, pyridine, and mixtures thereof.

Upon completion of the addition of acylating agent, the vigorously stirred reaction mixture is maintained at a temperature ranging between about 0° C. and about 30° C., preferably about room temperature (25° C.) until the reaction reaches completion as monitored by conventional means such as TLC analysis. The reaction mixture is then poured onto ice and extracted several times with a suitable solvent such as ethyl acetate, chloroform, methylene chloride, tetrahydrofuran, or a mixture of chloroform/methanol. A preferred solvent for this extraction is ethyl acetate. The extracts are then dried over a suitable drying agent, e.g., sodium sulfate, and the product may be purified by conventional means such as silica gel column chromatography.

Chromenylation of 7a was initially attempted employing 4,4-dimethyoxy-2-methylbutan-2-ol according to the literature method,[44,45] and only ca. 5% of 5a was detected by $^1H$ NMR. However, when 3-chloro-3-methyl-1-butyne was used,[47,55] 5a was obtained in 27% isolated yield (FIGS. 4 and 5). The same procedure on 7b afforded 5b in 73% yield. In contrast, no 5c could be detected when 7c was reacted with 3-chloro-3-methyl-1-butyne under the same conditions. Instead, a tripyranone derivative 9[56] was formed. The structure assignment of 9 was based on $^1H$ NMR and MS (FIG. 4). This indicated that the TBMDS-protecting group was lost during the course of chromenylation.

Hydrolysis of 5a to produce 6 under basic conditions proceeded smoothly. For example, conversion of 5a to 6 was uneventful with sodium bicarbonate in aq. MeOH in 44% yield (FIGS. 4 and 5). This represents a substantial yield improvement over previous methods for preparing 6. For instance, prior reported direct chromenylation of 2 with 4,4-dimethyoxy-2-methylbutan-2-ol furnished a mixture of product, with 6 being isolated in less than 10% yield.[55] Fries rearrangement on 5a or Friedel-Crafts reaction on 6 led to intermediate 4 which can then be converted to (+)-calanolide A and (−)-calanolide B (FIG. 1) using previously reported procedures.[44-46]

FIG. 5 illustrates preparation of (±)-calanolide A from 5a or 6. Thus, treatment of 2 using the inventive acylation method resulted in 7a. Chromenylation of 7a with 3-chloro-3-methyl-1-butyne resulted in 5a which can be converted directly to 4 via Fries rearrangement in the presence of $AlCl_3$. Alternatively, 4 may be obtained by the hydrolysis of 5a to yield 6, followed by a Friedel-Crafts reaction as discussed above.

The conversion of 5a to 4 under Fries rearrangement conditions is straightforward. A mixture of compound 5a with anhydrous aluminium chloride in an amount ranging from about 0.1 to about 20 moles, preferably about 10 moles, per mole of compound 5a is heated for a time period ranging between about 0.5 to about 6 hours, preferably about 2 hours at a temperature ranging between about 40° C. to about 250° C., preferably about 160° C. The mixture is then cooled to r.t. and treated with ice and hydrochloric acid to precipitate out the product. The precipitated product is taken into a suitable solvent, preferably ethyl acetate, and the aqueous solution is extracted with the same solvent. The extracts are combined and dried over any suitable drying agent, e.g., $Na_2SO_4$ and concentrated in vacuo. The crude product thus obtained may then be purified by any suitable means such as silica gel column chromatography using any suitable solvent or solvent mixtures, e.g., 25% ethyl acetate in hexane.

Compound 4 can be converted to 12-oxocalanolide 11 using a variety of reagents including chlorotitanium-mediated aldol reaction with acetaldehyde followed by the Mitsunobu reaction, and treatment with paraaldehyde or $CH_3CH(OEt)_2$ as described in U.S. Pat. Nos. 5,489,697; 5,869,324; 5,874,591; 5,840921; 5,847,164; 5,892,060; 5,872,264; 5,981,770; 5,977,385; 6,043,271; and co-pending application Ser. No. 09/173,143, filed Oct. 15, 1998 which are incorporated by reference in their entirety. Luche reduction of 11 with $NaBH_4$ and $CeCl_3(H_2O)_7$ yields (±)-calanolide A as described in U.S. Pat. Nos. 5,489,697; 5,869,324; 5,874,591; 5,840921; 5,847,164; 5,892,060; 5,872,264; 5,981,770; 5,977,385; 6,043,271; and co-pending application Ser. No. 09/173,143, filed Oct. 15, 1998.

FIG. 6 and FIG. 7 further illustrate preparation of (+)-calanolide A from compound 6. According to FIG. 6, a method for preparing (+)-calanolide A using 6 is provided. The introduction of the chiral side chains at the desired 7-position of 6 can be achieved using a variety of readily available chiral compounds 11[57-60] and 12. The latter compound, 12 (Z=H), is resulted from reduction of 11 (X=OH, Y=OMe) with $LiAlH_4$. The primary OH group in 12 (Z=H) is then selectively protected such that Z is, for example, t-butyldimethylsilyl (TBDMS), tetrahydropyran (THP), p-toluenesulfonyl (Ts) or $COR_{10}$ wherein $R_{10}$ represents $C_{1-6}$ alkyl, aryl-$C_{1-6}$ alkyl, mono- or poly-fluorinated $C_{1-6}$ alkyl, aryl or heterocycle. According to the method, 6 is coupled to compound 11 (X=OH) under Mitsunobu conditions ($PPh_3$, diethyl azodicarboxylate) to provide compound 13. Compound 13 is subsequently hydrolyzed to produce 13 (Y=OH). Compound 13 (Y=OH) is then subjected to an intramolecular Friedel-Crafts reaction to provide ketone (+)-10. Ketone (+)-10 is then subjected to Luche reduction to produce (+)-calanolide A 1.

The reaction of 6 with 11 (X=TsO) under nucleophilic substitution conditions also generates compound 13. Hydrolysis (NaOH, LiCl) of 13 (Y=OMe), or removal of the chiral auxiliary (LiOH or LiOOH) from 13 (Y=oxazolidinone), followed by intramolecular Friedel-Crafts cyclization, yields the chromanone (+)-10. Luche reduction of (+)-10 affords (+)-calanolide A. It should be noting that a substantial elimination from 11 (X=OH or TsO) occcured under both Mitsunobu and the nucleophilic substitution conditions, resulting in a requirement for excessive amount of the chiral moiety and a reduction in yield of 13.

In order to avoid the β-elimination from 11, a selectively protected chiral diol compound 12 is devised. Thus, Mitsunobu reaction ($PPh_3$, diethyl azodicarboxylate) of 6 with 12 (Z=TBDMS) leads to the formation of 14 (Z=H), followed by removal of TBDMS protecting group (FIG. 7). No β-elimination from 12 was observed in this process. Swern oxidation of 14 (Z=H) furnishes aldehyde derivative 13 (Y=H), which is further oxidized using $NaClO_2$ to form the carboxylic acid, 13 (Y=OH). As described in FIG. 6, intramolecular Friedel-Crafts cyclization on 13 (Y=OH) followed by Luche reduction yields (+)-calnolide A.

The synthetic sequence for (+)-calanolide A is extended to the synthesis of calanolide analogues (FIGS. 8 and 9). Thus, Pechmann reaction of phloroglucinol with various β-ketoesters yields substituted 5,7-dihydroxycoumarin 15. Selectively protecting the 7-hydroxy group leads to the formation of 16. Chromenylation of 16 can be achieved by reacting with β-hydroxyaldehyde dimethylacetal, providing chromenocoumarin 17, which is deprotected to furnish the free hydroxy group in 18. Mitsunobu reaction of 18 with 19 (X=OH), or nucleophilic substitution with 19 (X=TsO), followed by the hydrolysis, results in 20 (Y=OH). Intramolecular Friedel-Crafts cyclization on 20 (Y=OH) gives chromanone 21, which is reduced by NaBH4 to form the final calanolide analogues 22.

According to FIG. 8, 1,3,5-trihydroxybenzene was reacted with β-keto ester 25 under Pechmann conditions (See U.S. Pat. Nos. 5,489,697; 5,869,324; 5,874,591; 5,840921; 5,847,164; 5,892,060; 5,872,264; 5,981,770; 5,977,385; 6,043,271; and co-pending application Ser. No. 094173,143, filed Oct. 15, 1998, incorporated by reference in its entirety) to produce compound 15. The amount of β-keto ester 25 to 1,3,5-trihydroxybenzene generally ranges between about 1 to about 3, preferably about 1 per mole of 1,3,5-trihydroxybenzene. β-ketoester 25 is represented by the structure:

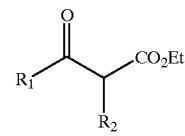

25 wherein $R_1$ is H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, $C_{1-6}$ alkoxy, amnino-$C_{1-8}$ alkyl, $C_{1-6}$ alkylamino, di($C_{1-6}$ alkyl)amino, $C_{1-8}$ alkylaino-$C_{1-8}$ alkyl, di($C_{1-6}$ alkyl) amino-$C_{1-8}$ alkyl, cyclohexyl, aryl, or heterocycle, wherein the aryl or the heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl)amino, amino-$C_{1-8}$ allyl, $C_{1-8}$ alkylamino-$C_{1-8}$ alkyl, di($C_{1-6}$ alkyl-amino-$C_{1-8}$ alkyl, nitro, azido or halogen; and $R_2$ is H, halogen, hydroxyl, $C_{1-6}$ alkyl, aryl-$C_{1-6}$ alkyl, mono- or poly-fluorinated $C_{1-6}$ alkyl, aryl or heterocycle. Compound 15 is represented by the structure:

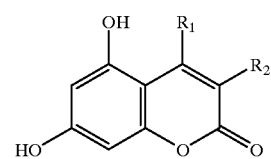

15 wherein $R_1$ and $R_2$ are as described above.

Thereafter, compound 15 is acylated with an acylating agent $(RCO)_2O$ under conventional acylation conditions to produce 16 wherein R represents $C_{1-6}$ alkyl, aryl-$C_{1-6}$ alkyl, mono- or poly-fluorinated $C_{1-6}$ alkyl, aryl or heterocycle.

The amount of acylating agent to compound 15 generally ranges between about 0.5 to about 6, preferably about 1 per mole of 15. Compound 16 is represented by the structure:

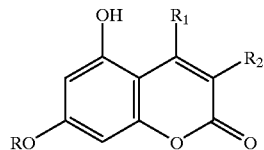

16 wherein R, $R_1$, and $R_2$ are as described above.

Compound 17 is produced by chromenylation of 16 with substituted β-hydroxyaldehyde dimethylacetal 26 under the reaction conditions described in U.S. Pat. Nos. 5,489,697; 5,869,324; 5,874,591; 5,840921; 5,847,164; 5,892,060; 5,872,264; 5,981,770; 5,977,385; 6,043,271; and co-pending application Ser. No. 09/173,143, filed Oct. 15, 1998, incorporated by reference in their entirety. Representative examples of substituted β-hydroxyaldehyde dimethylacetal 26 comprise:

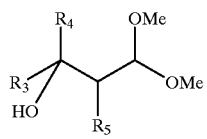

26 wherein $R_3$ and $R_4$ are independently selected from the group consisting of H, $C_{1-6}$ alkyl, aryl-$C_{1-6}$ alkyl, mono- or poly-fluorinated $C_{1-6}$ alkyl aryl or heterocycle; $R_3$ and $R_4$ can be taken together to form a 5–7 membered saturated cycle ring or heterocycle ring; and $R_5$ is H, halogen, methyl, ethyl. Compound 17 is represented by the structure:

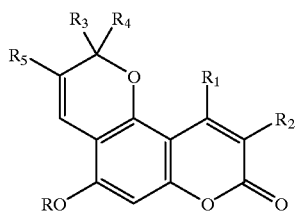

17 wherein R, $R_1$, $R_2$, $R_3$, $R_4$, and $R_5$ are as described above.

Thereafter, compound 17 is hydrolyzed to produce compound 18 under the basic hydrolysis conditions described above. Compound 18 is then coupled to 19 under Mitsunobu conditions to produce compound 20. Compound 19 is represented by the structure:

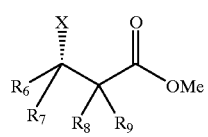

19 wherein $R_6$, $R_7$, $R_8$ and $R_9$ are independently selected from the group consisting of H, halogen, hydroxy, amino, mono- or dialkylamino-$C_{1-6}$ alkyl, aryl-$C_{1-6}$ alky, mono- or poly-fluorinated $C_{1-6}$ alkyl, hydroxy-$C_{1-6}$alkyl, amino-$C_{1-6}$ alkyl, aryl or heterocycle; or $R_6$ and $R_7$ together form a 5 to 7 membered cycle ring or heterocycle ring; or $R_8$ and $R_9$ together form a 5 to 7 membered cycle ring or heterocycle ring.

Compound 20 is represented by the structure:

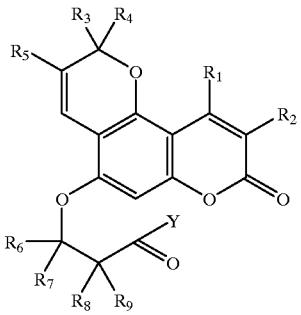

20 wherein $R_{1-9}$ are as described above and Y represents hydrogen, OH, or OMe.

Friedel-Crafts cyclization of 20 under conditions described above provides compound 21 which structure is represented below.

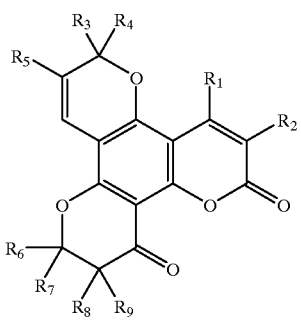

21 wherein $R_{1-9}$ are as described above.

Reduction of compound 21 using any suitable reagent, e.g., sodium borohydride, .results in calanolide analogue 22 whose structure is represented below.

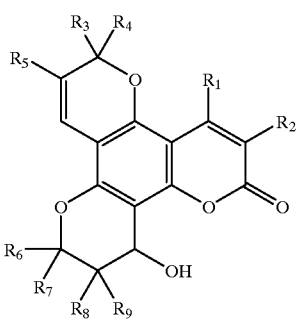

22 wherein $R_{1-9}$ are as described above.

Except as expressly defined otherwise, the following definition of terms is employed throughout this specification.

The terms "alkyl", "lower alkyl" or "$C_{1-6}$ alkyl" mean a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents listed below for aryl.

By "alkoxy", "lower alkoxy" or "$C_{1-6}$ alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

The term "halogen" includes chlorine, fluorine, bromine, and iodine, and their monovalent radicals.

The term "aryl" means an aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl), unsubstituted or substituted by 1 to 3 substituents selected from alkyl, O-alkyl and S-alkyl, OH, SH, —CN, halogen, 1,3-dioxolanyl, $CF_3$, $NO_2$, $NH_2$, $NHCH_3$, $N(CH_3)_2$, NHCO-alkyl, —$(CH_2)_mCO_2H$, —$(CH_2)_m$ $CO_2$-alkyl, —$(CH_2)_mSO_3H$, —NH alkyl, —N(alkyl)$_2$, —$(CH_2)_mPO_3H_2$, —$(CH_2)_mPO_3$(alkyl)$_2$, —$(CH_2)_mSO_2NH_2$, and —$(CH_2)_mSO_2NH$-alkyl wherein alkyl is defined as above and m is 0, 1, 2, or 3.

The term "cyclic ring" as referred to herein means a monocyclic or polycyclic moiety. By "polycyclic" is meant two or more rings that share two or more carbon atoms. A "carbocyclic group" which contains hetero atoms as one or more of its members can be referred to as a "heterocycle" or a "heterocyclic ring". Such a "heterocycle" can likewise be "monocyclic" or "polycylcic". A cyclic ring and a heterocyclic ring can be saturated, can contain one or more double bonds or can be aromatic. Each ring can be unsubstituted or substituted by 1 to 3 substituents selected from the group as described above for aryl.

The following examples are illustrative and do not serve to limit the scope of the invention as claimed. All references, patents and patent applications cited herein are hereby incorporated by reference in their entirety.

EXPERIMENTAL SECTION

General: Melting points were uncorrected. All commercial reagents and solvents were used without further purification. The $^1H$ NMR (300 MHz) and $^{13}C$ NMR (75 MHz) were run in indicated deuterated solvent and chemical shifts are reported in ppm with tetramethylsilane as the internal standard.

EXAMPLE 1

Determination of acylation conditions for the conversion of 2 to 7a

Due to the low yields from the Friedel-Crafts acylation reaction, a more practical procedure needed to be developed for the synthesis of 7a from 2. A variety of reaction conditions were investigated, which is summarized in Table I. Without Lewis acid such as $AlCl_3$ or base such as pyridine and 4-dimethylaminopyridine (DMAP), no reaction took place between coumarin 2 and propionyl anhydride (entries 1 and 2 in Table I). The reported conditions using $AlCl_3$[45] were repeated and led to 20% conversion of 2 to 7a, as indicated by HPLC analysis (entry 3). The best results were obtained when a catalytic amount of pyridine was used (entry 4), with 47% conversion to 7a along with a small amount of undesired diester 8a and some unreacted starting material 2. If pyridine was used as the solvent, a complex mixture of products was formed. The formation of the undesired diester 8a could be minimized by shortening the reaction time or lowering the reaction temperature, which, however, could also decrease the yield of the desired product 7a with increasing of the unreacted starting 2 (entry 5). On the other hand, prolonged reaction time or increasing the reaction temperature would increase the conversion of the starting material 2 to 7a, however, this was accompanied by an increase in the formation of undesired 8a and led to a more difficulty in purification of 7a. It appeared that DMAP might be too strong a base (entries 6 and 7) and proprionyl chloride too reactive an acylating agent (entry 8) for the selective acylation. Therefore, the pyridine promoted acylation was scaled up in a 50-gram scale reaction, affording 36% isolated yield of 7a. For introduction of a more bulky group at the 7-position of 2, a more reactive acylating agent such as acyl chloride can be used. For example, reaction between 2 and pivaloyl chloride at r.t. in the presence of pyridine yielded 7-monosubstituted 7b and 5,7-disubstituted 8b in isolated yields of 36% and 18%, respectively. It is worthwhile noting that reaction of 2 with 1.0 equivalent TBDMS-Cl in the presence of imidazole in DMF afforded 31% of 7-TBDMS substituted 7c, along with 24% of 5,7-bis(TBDMS) substituted 8c (FIG. 3).

TABLE I

Acylation of Coumarin 2 with Propionyl Anhydride to Form 7-monoester 7a

| Entry | Scale of 2 | Reaction Conditions | HPLC Yield of 7a |
|---|---|---|---|
| 1 | 2.5 g | in THF at 0° C. for 2 hr | no reaction |
| 2 | 2.5 g | in THF at 30° C. for 2 hr | no reaction |
| 3 | 5 g | $AlCl_3$ (2 eq.) in 1,2-dichloroethane at r.t for 24 hr | 20% |
| 4 | 2.5 g | pyridine (3 drops) in THF at r.t for 1.5 hr | 47% |
| 5 | 2.5 g | pyridine (3 drops) in THF at r.t for 1 hr | 26% |
| 6 | 5 g | 4-dimethylaminopyridine (0.1 eq.) in 1,2-dichloroethane at r.t for 4 hr | complicated results |
| 7 | 5 g | 4-dimethylaminopyridine (0.1 eq.) in 1,2-dichloroethane at 0° C. for 45 min | 47% isolated yield of 8a |
| 8 | 5 g | propionyl chloride in pyridine at 0° C. for 4 hrs | complicated results |

EXAMPLE 2

5-Hydroxy-7-propionyloxy-4-propylcoumarin (7a)

To a 2 L three-neck round-bottom flask equipped with a stir bar, additional funnel, $N_2$ inlet and outlet were added 50 g (2.27 mol) of 5,7-dihydroxy-4-propylcoumarin (2) and 500 mL of anhydrous THF. To this reaction mixture was added dropwise 33 g (2.27 mol) of propionic anhydride at r.t with stirring. After 90 min, the reaction was stopped and reaction mixture washed with 5% aq. $NaHCO_3$ solution. The organic layer was separated and washed with 1 N HCl and brine. The aqueous layers were extracted with dichloromethane. The organic layers were combined and washed with brine. After being dried over $Na_2SO_4$, the crude product was obtained from rotary evaporation and dried in vacuo to give 62 g crude product. TLC (1:1 Hexane/EtOAc) analysis indicated that the crude material contained the desired product (7a), starting compound 2 and a small amount of 5,7-diester 8a. The obtained crude product was then purified by silica gel column chromatography on a Biotage column eluting with 2:1 Hexane/EtOAc to give 12 g of 7a (36% yield) as white solid. mp: 166–168° C.; $^1H$ NMR (DMSO-$d_6$), 0.97 (3H, t, J=7.2 Hz), 1.14 (3H, t, J=7.4 Hz), 1.62 (2H, sextet, J=7.5 Hz), 2.62 (2H, q, J=7.5 Hz), 2.92 (2H, t, J=7.5 Hz), 6.09 (1H, s), 6.57 (1H, d, J=2.4 Hz), 6.67 (1H, d, J=2.4

Hz), 11.10 (1H, s); $^{13}$C NMR (CDCl$_3$), 8.6, 13.7, 22.4, 26.9, 37.2, 101.4, 105.3, 106.2, 111.9, 153.0, 155.9, 157.2, 158.0, 159.7, 172.2; IR (film): 3300-3075, 2968, 1758, 1676, 1610, 1433, 1126 cm$^{-1}$; MS m/e 277 (M+1); Anal. Calcd. for C$_{15}$H$_{16}$O$_5$: C, 65.21; H, 5.84. Found: C, 64.61; H, 5.86.

EXAMPLE 3

5-Hydroxy-7-pivaloyloxy-4-propylcoumarin (7b)

To a solution of coumarin 2 (1.10 g, 5 mmol) in THF (10 mL) was added pyridine (2.02 mL, 25 mmol), followed by pivaloyl chloride (0.612 mL, 5 mmol), and the reaction mixture was allowed to stir at room temperature for 6 days. The pyridinium hydrochloride was removed by filtration and washed a few times with ethyl acetate. The organic solutions were combined and washed, successively, with 1M HCl (2×25 mL), water (25 mL), aqueous saturated sodium bicarbonate (25 mL). After being dried over sodium sulfate and concentrated under vacuum, the crude product was purified by silica gel chromatography (8:1 hexane/ethyl acetate to 2:1 hexane/ethyl acetate) to obtain 8b (350 mg, 18% yield) and 7-pivaloylated coumarin 7b (550 mg, 36% yield) as a white solid. For compound 7b, mp: 158–160° C.; R$_f$=0.32 (4:1 hexane/ethyl acetate); $^1$H NMR (CDCl$_3$), 0.97 (3H, t, J=7.8 Hz), 1.37 (9H, s), 1.56 (2H, sextet, J=7.4 Hz), 2.84 (2H, t, J=7.8 Hz), 6.07 (1H, s), 6.43 (1H, d, J=2.4 Hz), 6.61 (1H, d, J=2.1 Hz), 8.09 (1H, s); $^{13}$C NMR (CDCl$_3$), 13.8, 22.4, 26.9, 37.8, 39.3, 102.4, 105.8, 107.2, 112.1, 153.3, 156.2, 156.3, 159.3, 161.9, 178.0; IR (film): 3358, 2971, 2365, 1730, 1615, 1431, 1275, 1146 cm$^{-1}$; MS m/e 305 (M+1); Anal. Calcd. for C$_{17}$H$_{20}$O$_5$: C, 67.09; H, 6.62. Found: C, 66.80; H, 6.70.

EXAMPLE 4

5,7-bis(pivaloyloxy)-4-propylcoumarin (8b)

To a solution of 5,7-dihydroxy-4-propylcoumarin (2) (1.10 g, 5 mmol) in pyridine (12 mL) and THF (6 mL) was added pivaloyl chloride (0.673 mL, 5.5 mmol) and the reaction mixture was allowed to stir at room temperature for 24 h. TLC revealed formation of a new less polar spot and unreacted starting material. In an effort to drive the reaction to completion, pivaloyl chloride (0.50 mL) was added and the reaction continued to stir at room temperature for another 72 h. The pyridinium hydrochloride was removed by filtration and washed a few times with ethyl acetate. The organic solutions were combined and washed, successively, with 1 M HCl (2×25 mL), water (25 mL), aqueous saturated sodium bicarbonate (25 mL). After being dried over sodium sulfate and concentrated under vacuum, the crude product was purified by silica gel chromatography (2:1 hexane/ethyl acetate) to obtain 8b as a white solid (1.90 g, 98% yield). mp 110–112° C.; R$_f$=0.49 (4:1 hexane/ethyl acetate); $^1$H-NMR (CDCl$_3$),: 1.03 (3H, t, J=7.8 Hz), 1.36 (9H, s), 1.41 (9H, s), 1.69 (2H, sextet, J=7.4 Hz), 2.81 (2H, t, J=7.8 Hz), 6.22 (1H, s), 6.60 (1H, d, J=2.4 Hz), 7.03 (1H, d, J=2.1 Hz); $^{13}$C-NMR (CDCl$_3$): 13.5, 20.7, 26.4, 26.8, 26.9, 36.4, 39.2, 39.4, 108.6, 111.5, 113.4, 114.2, 149.4, 152.7, 154.9, 155.4, 159.9, 177.1; IR (film): 3090, 2971, 2941, 2876, 1757, 1615, 1481, 1422, 1273 cm$^{-1}$; MS m/e 389 (M+1); Anal. Calcd. for C$_{22}$H$_{28}$O$_6$: C, 68.02; H, 7.26. Found: C, 67.77; H, 7.18.

EXAMPLE 5

7-TBDMS and 5,7-bis(TBDMS) Substituted Coumarin (7c and 8c)

A mixture of coumarin 2 (5.0 g, 23 mmol), TBDMS-Cl (5.8 g, 27 mmol), and imidazole (4.7 g, 69 mmol) in 50 ml of dry DMF was stirred at room temperature under nitrogen for 20 h, whereupon EtOAc (300 ml) was added to the reaction mixture. The precipitates formed were removed by filtration. The filtrate was washed, successively, with 1N HCl (100 mL×2), water (100 mL×3), and brine (200 mL). The organic layer was then dried with Na$_2$SO$_4$. After removal of the drying agent by filtration, the organic solution was kept at room temperature and crystals were formed. The solid was collected. The mother liquor was concentrated and the residue was recrystallized in EtOAc. This process was repeated two more times to give overall 2.2 g (28% yield) of 7c as white crystals. The residue from the mother liquor was further purified by column chromatography to give 2.5 g (24% yield) of solid that was assigned the structure of bis-TBDMS ether 8c, additional 0.2 g of 22 (combined yield of 31%), and 0.2 g of unreacted starting material 2. The analytical data of 7c were: mp 220–223° C.; $^1$H NMR (acetone-d$_6$) 0.28 (6H, s), 1.00 (12H, m), 1.69 (2H, m), 2.95 (2H, t, J=7.5 Hz), 5.91 (1H, s), 6.33 (1H, d, J=2.7 Hz), 6.42 (1H, d, J=2.4 Hz), 9.55 (1H, s); $^{13}$C NMR (DMSO-d$_6$) –4.7, –3.9, 13.7, 22.4, 25.4, 37.1, 99.2, 103.3, 103.5, 109.8, 156.7, 157.5, 158.4, 158.5, 160.1; IR 3497-3021 (s, broad), 1684 (s, sharp), 1616 (s, sharp) cm$^{-1}$; LRMS mle: 335 (M+1); Anal. Calcd. for C$_{18}$H$_{26}$O$_4$Si: C, 64.64; H, 7.83. Found: C, 64.31; H, 7.78. For 8c, mp 78–79° C.; $^1$H NMR 0.24 (6H, s), 0.36 (6H, s), 0.95–9.97 (21H, m), 1.59 (2H, q, J=7.5 Hz), 2.91 (2H, t, J=7.5 Hz), 6.02 (1H, s), 6.21 (1H, d, J=2.7 Hz), 6.48 (1H, d, J=2.4 Hz).

EXAMPLE 6

2,2-Dimethyl-5-propionyloxy-10-propyl-2H,8H-benzo[1,2-b:3,4-b']dipyran-8-one (5a)

To a solution of 7-propionate 7a (0.83 g, 3.0 mmol) in 2-butanone (40 mL) and DMF (4 mL) were added tetrabutylammonium iodide (1.11 g, 3 mmol), K$_2$CO$_3$ (1.04 g, 7.5 mmol), and 3-chloro-3-methyl-1-butyne (1.11 g, 3 mmol). The reaction mixture was heated at 60° C. for 1 h before ZnCl$_2$ (3.9 mL of 1.0 M solution in ether, 3.9 mmol) was added. The temperature was then raised to 70° C. and maintained at that temperature for 21 h. The reaction mixture was cooled to room temperature and quenched with saturated aqueous NH$_4$Cl (100 mL). The mixture was extracted with EtOAc (100 mL×2) and the combined organic layers were washed with brine (100 mL) and dried over Na$_2$SO$_4$. Evaporation of the solvent gave the crude product (1.9 g). After column chromtographic purification, 280 mg (27.1% yield) of the desired product 5a was obtained as a waxy solid. $^1$H NMR (DMSO-d$_6$) 1.00 (3H, t, J=7.2 Hz), 1.16 (3H, t, J=7.5 Hz); 1.47 (6H, s), 1.61 (2H, m), 2.71 (2H, q, J=7.5 Hz), 2.89 (2H, t, J=7.8), 5.84 (1H, d, J=9.9 Hz), 6.17 (1H, s), 6.41 (1H, d, J=10.2 Hz); $^{13}$C NMR (DMSO-d$_6$) 8.6, 13.7, 22.8, 26.6, 27.2, 37.4, 78.3, 103.6, 107.2, 110.8, 113.4, 115.5, 130.1, 148.5, 151.4, 154.4, 156.9, 159.3, 172.2; IR 1767 (s and sharp), 1723 (s and sharp), 1616 (s and sharp) cm$^{-1}$; MS m/e 343 (M+1); Anal. Calcd. for C$_{20}$H$_{22}$O$_5$: C, 70.16; H, 6.47. Found: C, 70.37; H, 6.51.

EXAMPLE 7

2,2-Dimethyl-5-pivaloyloxy-10-propyl-2H,8H-benzo[1,2-b:3,4-b']dipyran-8-one (5b)

To a suspension of compound 7b (304 mg, 1 mmol) in 2-butanone (13 mL) and DMF (1.3 mL) was added potassium carbonate (346 mg, 2.5 mmol), 3-chloro-3-methyl-1-butyne (0.56 mL, 5 mmol) and tetrabutylammonium iodide (360 mg, 1 mmol). The reaction mixture was heated to 60°

C. for 1 h, then anhydrous $ZnCl_2$ (1.0 M solution in ether, 1.3 mL) was added. The reaction mixture was heated to 70° C. for 26 h, then cooled to r.t., quenched with saturated aqueous $NH_4Cl$ (25 mL), and extracted with ethyl acetate (2×75 mL). The organic solutions were combined, washed with brine, dried ($Na_2SO_4$), and concentrated. The crude product obtained was purified by silica gel chromatography (8:1 hexane/ethyl acetate) to obtain 5b as a yellow solid (270 mg, 73%). mp: 65–68° C.; $R_f$: 0.54 (4:1 hexane/ethyl acetate); $^1$H NMR ($CDCl_3$) 1.04 (3H, d, J=7.2 Hz), 1.39 (9H, s), 1.52 (6H, s), 1.66–1.71 (2H, m), 2.90 (2H, t, J=7.8 Hz), 5.62 (1H, d, J=10.2 Hz), 6.07 (1H, s), 6.30 (1H, d, J=10.2 Hz), 6.62 (1H, s); $^{13}$C NMR ($CDCl_3$) 13.8, 22.9, 26.9, 27.8, 38.3, 39.3, 78.1, 103.5, 107.9, 110.9, 113.4, 115.9, 129.1, 148.9, 152.0, 155.1, 157.4, 160.6, 176.2; IR (film): 2967, 1750, 1616, 1364, 1142 $cm^{-1}$; MS m/e 371 (M+1); Anal. Calcd. for $C_{22}H_{26}O_5$: C, 71.33; H, 7.07. Found: C, 71.08; H, 7.35.

EXAMPLE 8

2,2-Dimethyl-5-hydroxy-10-propyl-2H,8H-benzo[1, 2-b:3,4-b']dipyran-8-one (6)

To a solution of ester 5a (223 mg, 0.65 mmol) in 15 mL of MeOH were added saturated aqueous solution of $NaHCO_3$ (7 mL) and water (7 mL). The reaction mixture was stirred at room temperature under nitrogen for 7 h until TLC indicated complete consumption of the starting material. The reaction mixture was then acidified with 10% aqueous HCl (100 mL), and extracted with EtOAc (50 mL). The organic solution was washed with brine (100 mL) and dried with $Na_2SO_4$. Evaporation of the solvent yielded the crude product that was purified by preparative TLC to afford 97 mg (52% yield) of 6 as a solid. mp 190–192° C.; $^1$H NMR (DMSO-$d_6$) δ 0.99 (3H, t, J=7.3 Hz), 1.45 (6H, s), 1.59 (2H, m), 2.83 (2H, t, J=7.6 Hz), 5.66 (1H, d, J=9.9 Hz), 5.92 (1H, s), 6.34 (1H, s), 6.57 (1H, d, J=9.9 Hz), 10.77 (1H, s); $^{13}$C NMR (DMSO-$d_6$) δ 13.7, 22.9, 27.2, 37.5, 77.5, 95.7, 102.2, 106.1, 109.9, 116.3, 127.1, 151.7, 155.7, 156.4, 157.8, 160.0, 188.9; IR (film): 3185, 1686, 1582, 1381, 1157 $cm^{-1}$; MS m/e: 287 (M+1); Anal. Calcd. for $C_{17}H_{18}O_4$: C, 71.31; H, 6.34. Found: C, 71.39; H, 6.40.

EXAMPLE 9

Conversion of 5a to 4 under Fries Rearrangement Conditions

A mixture of compound 5a (1 g, 2.9 mmol) with anhydrous aluminium chloride (5 g,, 37.5 mmol) is heated for 2h at 160° C. The mixture is then cooled to r.t. and treated with ice and hydrochloric acid (1 N, 5 mL). The precipitated product is taken into ethyl acetate and the aqueous solution is extracted with the same solvent (80 mL×3). The combined ethyl acetate solution is dried over $Na_2SO_4$ and concentrated in vacuo. The crude product thus obtained is chromatographed on a silica gel column eluting with 25% ethyl acetate in hexane to afford compound 4 (0.5 g, 50% yield).

EXAMPLE 10

Conversion of 6 to 4 under Friedel-Crafts Conditions

A mixture of compound 6 (1 g, 3.5 mmol) and anhydrous aluminium chloride (0.9 g,, 7 mmol) in 1,2-dichloroethane (10 mL) is heated to 75° C. for 30 min, into which was added dropwise a mixture of propionyl anhydride (0.5 g, 3.5 mmol) and anhydrous aluminium chloride (0.9 g, 7 mmol) in 1,2-dichloroethane (5 mL). The resulting mixture is heated at 75° C. for an additional hour. After the mixture is allowed to be cooled to r.t., it is quenched with ice and 1 N HCl (5 mL). The precipitated product is taken into ethyl acetate and the aqueous solution is extracted with the same solvent (80 mL×3). The combined ethyl acetate solution is dried over $Na_2SO_4$ and concentrated in vacuo. The crude product thus obtained is recrystallized from acetone to afford compound 4 (0.5 g, 50% yield).

EXAMPLE 11

Conversion of 4 to 11 (12-oxocalanolide)

A solution containing chromene 4 (344 mg, 1.0 mmol), acetaldehyde diethylacetal (473 mg, 4.0 mmol), trifluoroacetic acid (1.5 mL, 19.4 mmol) and anhydrous pyridine (0.7 mL) was heated at 140° C. under $N_2$. The reaction was monitored by TLC analysis. After 4 hours, the reaction mixture was cooled to room temperature, diluted with ethyl acetate and washed several times with 10% aqueous $NaHCO_3$ and brine. The organic layer was separated and dried over $Na_2SO_4$. The solvent was removed in vacuo and the crude product was purified by silica gel column chromatography eluting with ethyl acetate/lexane (2:3). Chromanone (±)-11 (10,11-trans-dihydro-4-propyl-6,6,10,11-tetramethyl-2H,6H, 12H-benzo[1,2-b:3,4-b':5,6-b"]-tripyran-2,12-dione) (110 mg, 30% yield) was obtained m.p. 176–177° C. (Lit.[45] 130–132° C.). $^1$HNMR[45] ($CDCl_3$) δ 1.02 (3H, t, J=7.5 Hz, $CH_3$); 1.21 (3H, d, J=6.8 Hz, $CH_3$); 1.51 (3H, d, J=7.0 Hz, $CH_3$); 1.55 (6H, 2s, $2CH_3$); 1.63 (2H, sexet, J=7.0 Hz, $CH_2$); 2.55 (1H, dq, J=6.9 Hz, J=11.0 Hz, $H_{11}$); 2.88 (2H, t, J=7.6 Hz, $CH_2$); 4.28 (1H, dq, J=6.3 Hz, J=11.0 Hz, $H_{10}$); 5.60 (1H, d, J=9.9 Hz, $H_7$); 6.04 (1H, s, $H_3$); 6.65 (1H, d, J=11.8 Hz, $H_8$); MS (CI): 369 (100, M+1).

EXAMPLE 12

Preparation of (±)-Calanolide A

To a solution of chromanone (±)-11 (11 mg, 0.03 mmol) in ethanol (0.4 mL) was added sodium borohydride (2.26 g, 0.06 mmol) and $CeCl_3(H_2O)_7$ (11.2 mg, 0.03 mmol) in ethanol (5 mL) at room temperature. After stirring for 45 minutes, the mixture was diluted with $H_2O$ and extracted with ethyl acetate. The organic layer was dried over $Na_2SO_4$ and concentrated. The crude product was purified by preparative TLC eluting with ethyl acetate/hexane (1:1) to afford (±)-calanolide A (1) (10.5 mg, 94%). m.p. 52–54° C., which increased to 102° C. after it was dried thoroughly (Lit[45]. 56–58° C.). $^1$H NMR ($CDCl_3$): δ 1.03 (3H, t, J=7.3 Hz, $CH_3$), 1.15 (3H, d, J=6.8 Hz, $CH_3$), 1.46 (3H, d, J=6.8 Hz, $CH_3$), 1.47 (3H, s, $CH_3$), 1.51 (3H, s, $CH_3$), 1.66 (2H, m, $CH_2$), 1.93 (1H, m, $H_{11}$), 2.89 (2H, m, $CH_2$), 3.52 (1H, broad-s, OH), 3.93 (1H, m, $H_{10}$), 4.72 (1H, d, J=7.8 Hz, $H_{12}$), 5.54 (1H, d, J=10.0 Hz, $H_7$), 5.94 (1H, s, $H_3$), 6.62 (1H, d, J=9.9 Hz, $H_8$); MS (CI): 371 (75.4, M+1), 370 (16.1, $M^+$), 353 (100, M-OH); Anal. calcd. for $C_{22}H_{25}O_5$: C, 71.33; H, 7.07; Found: C, 71.63; H, 7.21.

EXAMPLE 13

Synthesis of Methyl 3-Hydroxy-2-methylbutyrate 11 (X=OH, Y=OMe) from D-Threonine According to the Literature Method[57]

An aqueous solution of D-threonine (5.95 g in 50 ml water) was treated with 48% aqueous HBr (10 ml) and KBr (21.0 g). The mixture was cooled to −15° C. and NaNO$_2$ (3.8 g) was slowly added in small portions over 2.5 h. After overnight stirring while the temperature was warmed up to room temperature (3×150 mL), the mixture was extracted with ether. The ether solution was dried (Na$_2$SO$_4$) and concentrated in vacuo to give the crude bromoacid as an oil. The bromoacid was dissolved in absolute EtOH (75 mL) and cooled to −30° C. A solution of KOH (5.05 g) in ethanol (40 mL) was added slowly, and the reaction mixture was stirred overnight while the temperature was allowed to warm up to room temperature. The solid KBr was removed by filtration and the filtrate was concentrated under reduced pressure. The residue was transferred to a solution of 18-crown-6 (10.55 g) in methylene chloride (100 mL). Dimethyl sulfate (3.56 g) was added to the reaction mixture and stirring was continued for 2 h. Ether was added and the precipitate formed was filtered off. The volatile solvent was removed by simple distillation to give crude epoxide that still contained the crown ether (1.3 g): 1H NMR (CDCl$_3$) 1.39 (3H, d, J=5.1 Hz),3.30 (1H, m),3.52(1H, d, J=4.5 Hz),3.81(3H, s).

A solution of MeLi in ether (21.7 mL of 1.4 M solution) was added to a stirred suspension of CuI (3.07 g) in ether (30 mL) at −30° C. After 15 min of stirring, a solution of the crude epoxide (1.3 g) in ether (24 mL) was added to the reaction mixture. The mixture was stirred for 2 h before a solution of concentrated ammonium hydroxide in saturated ammonium chloride was added. The resulting biphasic solution was extracted with EtOAc and the combined organic solution was dried and the solvent was removed by simple distillation to give a complex mixture (0.26 g) that might contain 11 (X=OH, Y=OMe) as a yellow oil.

EXAMPLE 14

Synthesis of 3-Hydroxy-2-methylbutyric Acid 11 (X=OH, Y=OH) from Ethyl 2-methylacetoacetate According to the Literature Method[58,59]

To a 6 L Erlenmeyer flask containing Baker's yeast (100 g) and sucrose (150 g) was added tap water (1000 mL) and the reaction mixture was mechanically stirred at room temperature for 0.5 h. Ethyl 2-methylacetoacetate (10 g, 0.0694 mol) was added to the reaction mixture and stirring continued for 24 h. Sucrose (50 g) was added and stirring continued for another 24 h. Hyflo super cel (50 g) was added to the reaction mixture and filtered through a sintered glass funnel. The aqueous solution was then extracted with ether (1.5 L), dried over sodium sulfate, and filtered. The solvent ether was removed via simple distillation to obtain ethyl 3-hydroxy-2-methylbutyrate (10 g, 100%) as a mixture of two isomers: $^1$H NMR (CDCl$_3$) δ 1.18–1.30 (18H, m), 2.47–2.52 (2H, m), 3.85–3.91 (1H, m), 4.05–4.10 (1H, m), 4.13–4.21 (4H, m).

To ethyl 2-methyl-3-hydroxybutyrate obtained above (10 g, 0.0694 mol) was added 30% aqueous sodium hydroxide (40 mL), and the mixture was stirred at room temperature for 4 h. The reaction mixture was concentrated under vacuum to obtain a yellow solid. The solid was dissolved in 1M HCl (100 mL) and extracted with ether (3×100 mL), dried over sodium sulfate and concentrated under vacuum to obtain 3-hydroxy-2-methyl butyric acid (2.0 g, 24%) as a mixture of diastereomers. For the major isomer: $^1$H NMR (CDCl$_3$) δ 1.21–1.24 (6H, m), 2.57–2.62 (1H, m), 4.11–4.15 (1H, m).

EXAMPLE 15

Synthesis of Oxazolidinone 11 (X=OH, Y=Oxazolidinone) according to the Literature Method[60]

A 7 ml freshly prepared LDA (0.5 M in hexane-ether) was cooled at −78° C., and to this solution was added dropwise Evan's oxazolidinone in 20 ml ether. The reaction was stirred for 30 min, followed by the dropwise addition of chlorotitanium triisopropoxide (9 ml 1.0M in hexane, 3 mmol) at −78° C. The solution was allowed to warm up to −40° C. over 1 h then cooled down to −78° C. Acetaldehyde was added in one portion via a cold syringe. The temperature was maintained between −78° C.~−40° C. under nitrogen for 3 h. Saturated aqueous solution of NH$_4$Cl (5 mL) was added. After filtration and extraction, the crude product (690 mg) was purified by column chromatography to afford 429 mg (62.4%) product 11 (X=OH, Y=Oxazolidinone) as an oil: $[α]_D$=+154.0° (c 0.5, MeOH); $^1$H NMR (CDCl$_3$) 0.91 (3H, d, J=6.6 Hz), 0.93 (3H, d, J=7.2 Hz), 1.17 (3H, d, J=6.9 Hz), 1.22 (3H, d, J=6.6 Hz), 2.38 (1H, m,), 3.90 (1H, dq J=3,6,6.5 Hz), 4.16 (1H, ddd, J=3.3,6.4, 12.9 Hz), 4.23 (1H, dd, J=3.2,9.0 Hz), 4.29 (1H, apparent t, J=8.6 Hz), 4.47 (1H, m); $^{13}$C NMR (CDCl$_3$) 10.5, 14.6, 17.8, 19.2, 28.5, 42.8, 58.6, 63.3, 68.5, 154.3, 176.6; IR 3302–3650 (m, broad), 1780 (s, sharp), 1699(s, sharp) cm$^{-1}$; LRMS cacld for C$_{11}$H$_{19}$NO$_4$ 229.3, found 229.9. Anal. Calcd for C$_{11}$H$_{19}$NO$_4$: C, 57.6; H, 8.4; N, 6.1. Found: C, 57.78; H 8.38; N, 6.07.

EXAMPLE 16

Synthesis of Oxazolidinone 11 (X=OTs, Y=Oxazolidinone)

Alcohol 11 (X=OH, Y=Oxazolidinone) (242 mg, 1.06 mmol) was dissolved in 2 mL pyridine, and the solution was stirred at −20° C. while TsCl (262 mg, 1.38 mmol) was added quickly under nitrogen. The temperature was allowed to rise to room temperature. Stirring was continued for 42 h. Water (5 ml) was added slowly at −20° C. then the reaction was stirred for 40 min and diluted with 10 ml EtOAc. The two layers were separated and the organic layer was washed with 1N HCl (10 mL×3), brine (10 mL), and dried with sodium sulfate. Evaporation of the solvent in vacuo afforded crude tosylate 11 (X=OTs, Y=Oxazolidinone) (192 mg). After preparative TLC purification, 92 mg (23%) of product was obtained as an oil: $^1$H NMR (CDCl$_3$) δ ppm, 0.90 (6H, t, J=6.6 Hz), 1.13 (3H, d, J=7.2 Hz), 1.30 (3H, d, J=6.6 Hz), 2.33 (1H, m), 2.44 (1H, m), 3.98 (1H, m), 4.21–4.29 (2H, m), 4.44 (1H, m), 5.00 (1H, m); $^{13}$C NMR δ 12.9, 14.4, 17.9, 19.1, 21.5, 28.2, 42.9, 58.6, 63.2, 79.6, 127.9, 129.8, 134.4, 144.7, 153.9, 173.2. Anal. Calcd. for C$_{18}$H$_{25}$O$_6$SN: C, 56.38; H, 6.57; N, 3.65; Found: C, 56.12; H, 6.64; N, 3.51.

EXAMPLE 17

Synthesis of 1,3-Dihydroxy-2-methylbutane 12 (Z=H)

To ethyl 3-hydroxy-2-methylbutyrate (7.3 g, 50 mmol) in ether (250 mL) at 0° C., added LiAlH$_4$ (5.9 g, 155.5 miol). The gray solution was stirred at 0° C. for 10 minutes, cooling bath removed and stirring continued at room temperature for 6 h. The reaction mixture was cooled to 0° C. and quenched slowly by dropwise addition of water (6 mL), 1M NaOH (6 mL), water (6 mL). Excess MgSO$_4$ (100 g) was added to the reaction mixture and allowed to stir at room temperature overnight. Filtered the reaction mixture and washed the solid with ether (400 mL). The ether extracts was concentrated under vacuum to obtain 1,3-dihydroxy-2-methylbutane 12 (Z=H) (2.6 g, 50%) as a yellow oil. $^1$H-NMR (CDCl$_3$) δ 0.89 (3H, d, J=6.9 Hz), 1.19 (3H, d, J=6.6 Hz), 1.81 (1H, m), 3.70 (2H, m), 4.04 (11H, m); MS[M-1]+103.5.

EXAMPLE 18

Synthesis of the Protected 1,3-Dihydroxy-2-methylbutane 12 (Z=TBDMS)

To a suspension of sodium hydride (424 mg, 10.6 mmol) in THF (30 mL) added 12 (Z=H) (1.1 g, 10.6 mmol) and stirred at room temperature for 45 min, at which time a large amount of an opaque white precipitate had formed. The tert-butyldimethylsilyl chloride (1.59 g, 10.6 mimol) was added and the reaction mixture was allowed to stir at room temperature for 1.5 h. The reaction mixture was diluted with ether (300 mL) and washed with 10% aqueous potassium carbonate (90 mL), brine (75 mL). The organic extracts were dried over sodium sulfate, concentrated under vacuum and purified by silica gel chromatography (8/1 hexane/ethyl acetate) to obtain 12 (Z=TBDMS) (2.3 g, 99%) as a colorless oil. $^1$H NMR (CDCl$_3$) δ 0.08 (6H, s), 0.90 (12H, s,d), 1.16 (3H, d, J=6.3 Hz), 3.72 (2H, m), 3.99 (1H, m); $^{13}$C NMR (CDCl$_3$) δ −5.8 (2C), 10.5, 19.5, 25.7, 25.9, 39.8, 70.7; Anal. Calcd for C$_{11}$H$_{25}$O$_2$Si: C, 60.55; H, 11.93. Found C, 61.01; H, 11.84; IR (film): 3449, 2957, 2859, 1464, 1256 cm$^{-1}$; MS [M+1]$^+$219.1.

Compound 14 (Z=TBDMS)

To monophenol 6 (900 mg, 3.14 mmol), txiphenylphosphine (1.24 g, 4.73 mmol) and 12 (R=TBDMS) (1.1 g, 5.05 mmol) in THF (60 mL) added DEAD (800 μL, 5.08 mmol) and stirred at room temperature under nitrogen overnight. The reaction mixture was concentrated under vacuum and purified by silica gel chromatography (3/1 hexane/ethyl acetate) to obtain 14 (Z=TBDMS) (1.53 g, 100%) as an oil. $^1$H NMR (CDCl$_3$) δ −0.08 (6H, m), 0.88 (9H, s), 0.96 (3H, d, J=7.2 Hz), 1.03 (3H, t, J=7.2 Hz), 1.27 93H, d, J=6.3 Hz), 1.49 (6H, s), 1.66 (2H, m), 2.08 (1H, m), 2.88 (2H, t, J=7.6 Hz), 3.56 (2H, m), 4.51 (1H, m), 5.52 (1H, d, J=9.9 Hz), 5.94 ((1H, s), 6.42 (1H, s), 6.64 (1H, d, J=9.9 Hz); $^{13}$C-NMR (CDCl$_3$) δ −5.7 (2C), 11.9, 14.0, 15.4, 18.1, 23.1, 25.8 (3C), 27.7 (2C), 38.3, 40.3, 64.6, 65.4, 75.2, 94.2, 103.7, 107.8, 110.8, 116.9, 126.7, 151.9, 156.3, 158.2, 161.4; Anal. Calcd for C$_{28}$H$_{42}$O$_5$Si: C, 69.03; H, 8.63. Found C, 69.33; H, 8.84; IR (film): 2928, 2857, 1738, 1605 cm$^-$; MS [M+1]$^+$487.2.

EXAMPLE 19

Compound 14 (Z=H)

To 14 (Z=TBDMS) (1.5 g, 3.08 mmol) in THF (45 mL) added TBAF (1.0 M soln in THF, 5 mL, 5 nmmol) and stirred at room temperature overnight. The reaction mixture was acidified with 1M HCl and extracted with ethyl acetate. The organic extracts were then washed with water, brine, dried (sodium sulfate) and concentrated under vacuum. The crude product was purified by silica gel chromatography (1/1 hexane/ethyl acetate) to obtain 14 (Z=H) (800 mg, 70%) as an oil. $^1$H-NMR (CDCl$_3$) δ 0.87 (3H, d, J=7.8 Hz), 1.06 (3H, t, J=6.9 Hz), 1.32 (3H, d, J=6.3 Hz), 1.49 (6H, s), 1.65 (2H, m,), 2.09 (1H, m), 2.88 (2H, t, J=7.6 Hz), 3.68 (2H, d, J=5.7 Hz), 4.50 (1H, m), 5.53 (1H, d, J=9.9 Hz), 5.95 (1H, s), 6.4 (1H, s), 6.62 (1H, d, J=10.2 Hz); 13C-NMR (CDCl$_3$) δ 12.4, 13.9, 16.2, 23.1, 27.7 (2C), 38.3, 40.4, 65.0, 75.0, 94.2, 104.0, 107.8, 110.9, 116.6, 126.9, 151.9, 156.0, 156.5, 158.2, 161.4; Anal. Calcd for C$_{22}$H$_{28}$O$_5$+0.7 eq H2O: C, 68.62; H, 7.70. Found C, 68.71; H, 7.85; IR (film): 3464, 2969, 2874, 1738, 1593 cm$^{-1}$; MS [M+1]$^+$373.1.

EXAMPLE 20

Compound 13 (Y=H)

To CH$_2$Cl$_2$ (1 mL) at −78° C. added oxalyl chloride (20 μL, 0.223 mmol), followed by DMSO (33 μL, 0.459 nunol). After 5 minutes added alcohol 14 (R=H) (57 mg, 0.153 mmol) in CH$_2$Cl$_2$ (2 mL). The reaction mixture was stirred at −78° C. for 30 minutes. Triethylamine (107 μL, 0.765 mmol) was added to the reaction mixture and allowed to warm to room temperature over 2 h. The reaction mixture was concentrated under vacuum and purified by silica gel chromatography to obtain 13 (Y=H) (46 mg, 82%) as an oil. $^1$H-NMR (CDCl$_3$) δ 1.03 (3H, t, J=7.2 Hz), 1.21 (3H, d, J=6.9 Hz), 1.28 (3H, d, J=6.9 Hz), 1.49 (6H, s), 1.55–1.70 (2H, m), 2.72–2.77 (1H, m), 2.89 (2H, t, J=7.2 Hz), 4.72 (1H, m), 5.52 (1H, d, J=10.2 Hz), 5.97 (1H, s), 6.42 (1H, s), 6.55 (1H, d, J=10.2 Hz), 9.79 (1H, d, J=2.4 Hz); MS [M+1]$^+$371.2.

EXAMPLE 21

Compound 13 (Y=OH)

To aldehyde 13 (Y=H) (43 mg, 0.116 mmol) in acetone (4 mL) added 2-methyl-2-butene (1 mL, 2.0 M solution in THF). To the above reaction mixture added sodium chlorite (100 mg, 1.10 mmol) and sodium dihydrogenphosphate (96 mg, 0.800 mmol) in water (2 mL) and allowed to stir at room temperature overnight. The reaction mixture was diluted with water and extracted with ethyl acetate, dried (Na$_2$SO$_4$) and concentrated under vacuum to obtain 13 (Y=OH) (45 mg, 100%) as an oil. $^1$H-NMR (CDCl$_3$) δ 1.04 (3H, t, J=7.2 Hz), 1.22 (3H, d, J=6.9 Hz), 1.27 (3H, d, J=6.9 Hz), 1.49 (6H,s), 1.52–1.67 (2H, m), 2.86–2.93 (3H, m), 4.73 (1H, m), 5.52 (1H, d, J=9.9 Hz), 5.97 (1H, s), 6.45 (1H, s), 6.61 (1H, d, J=9.9 Hz); MS [M+1]+387.2.

EXAMPLE 22

12-Oxocalanolide A (10) from 13 (Y=OH)

To acid 13 (Y=OH) (120 mg, 0.31 mmol) in benzene (3 mL) added thionyl chloride (90 μL, 1.24 mmol) and refluxed under nitrogen for 1 h. The reaction mixture was cooled to room temperature and concentrated under vacuum. The residue was dissolved in CH$_2$Cl$_2$ and concentrated under vacuum. This process was repeated twice. The reaction mixture was then dissolved in xylene (3 mL). Nafion NR-50 (50 mg) was added to the reaction mixture and refluxed for 22 h. Cooled to room temperature, filtered the resin, diluted with ethyl acetate and washed with aqueous saturated sodium bicarbonate solution and brine. The organic extracts were dried over sodium sulfate and concentrated under vacuum. The crude product was then purified by preparative TLC (10% ethyl acetate in hexanes) to obtain 10 (20 mg, 18%).

EXAMPLE 23

Compound 19 (R$_6$=R$_8$=R$_9$=H, R$_7$=Me, X=OTs)

A solution of methyl acetoacetate (20 g, 0.17 mol) in MeOH (100 ml) was added dropwise to a stirred solution of NaBH$_4$ (2 g, 0.05 mmol) in MeOH (200 ml) at room temperature. The reaction was monitored by TLC. After 1 hour of stirring, no reaction occurred. An additional 1 g (0.03 mol) of NaBH$_4$ was added into the reaction mixture, and another portion of NaBH$_4$ (1 g, 0.03 mol) after 0.5 h of stirring. Stirring was continued for 0.5 hour, and no starting compound was detected by TLC. The MeOH was removed to afford a residue as a clear oil. The residue was washed with 1N HCl (150 ml), then extracted into EtOAc (3×200 ml). The combined organic layers were washed with brine, dried over Na$_2$SO$_4$, and concentrated to afford 13 g of crude product methyl 3-hydroxybutyrate as a light-yellow oil which was used for the following tosylation without fuirther purification.

To a solution of methyl 3-hydroxybutyrate (13 g, 110 mmol) in anhydrous pyridine (100 ml) was added p-toluenesulfonyl chloride (31.5 g, 165 mmol) at 0° C. under $N_2$. After two days of stirring at 0° C., the reaction mixture was cooled to −5° C. followed by the dropwise addition of water (100 ml) while maintaining the temperature <0° C. After an additional 10 min of stirring,more water (200 ml) was added slowly. Crystallization occurred immediately. The temperature was maintained at 0° C. for 1 h, and the crystalline product was filtered, washed with water (5×100 ml), and dried to give 20.6 g (70%) of 19 ($R_6=R_8=R_9=H$, $R_7=Me$, X=OTs) as a white solid: mp. 45–47° C.; $^1H$ NMR ($d_6$-DMSO) δ 1.27 (3H, d, J=6.6 Hz), 2.43 (3H, s), 2.61 (1H, dd, J=15.0, 7.5 Hz), 2.69 (1H, dd, J=15.0, 5.4 Hz), 3.48 (3H, s), 4.86 (1H, m), 7.48 (2H, d, J=8.1 Hz), 7.78 (2H, d, J=8.1 Hz); $^{13}C$ NMR (CDCl$_3$) δ 20.4, 21.1, 40.5, 51.6, 76.8, 127.6, 130.3, 133.6, 145.0, 169.7; IR 1750 cm$^{-1}$. Anal. Calcd for $C_{12}H_{16}O_5S$: C, 52.94; H, 5.88. Found: C 53.10; H 5.95.

EXAMPLE 24

Compound 20 ($R_1$=n-propyl, $R_2=R_5=R_6=R_7=H$, $R_3=R_4=R_8=R_9=Me$, Y=OH)

To monophenol 6 (430 mg, 1.50 mmol), triphenylphosphine (590 mg, 2.25 mmol) and 19 ($R_6=R_7=H$, $R_8=R_9=Me$, X=OH) (396 mg, 3 mmol) in dioxane (34 mL) added DEAD (360 μL, 2.25 mmol) and stirred at reflux under nitrogen for 2 h. The reaction mixture was cooled and concentrated under vacuum. The residue was dissolved in ethyl acetate (100 mL) and washed with water (80 mL), dried (sodium sulfate), concentrated under vacuum and purified by silica gel chromatography (3/1 hexane/ethyl acetate) to obtain the corresponding methyl ester of 20 (445 mg, 74%) as a white solid. Mp: 100–101° C.; $^1H$ NMR (DMSO-d$_6$) δ 0.99 (3H, t, J=7.5 Hz), 1.26 (6H, s), 1.45 (6H, s), 2.39 (2H, m), 2.86 (2H, t, J=7.5 Hz), 3.63 (3H, s), 4.09 (2H, s), 5.73 (1H, d, J=10.2 Hz), 6.02 (1H, s), 6.45 (1H, d, J=9.6 Hz), 6.63 (1H, s); $^{13}C$-NMR (CDCl$_3$) δ 13.8, 22.3, 23.0, 27.7, 38.3, 43.2, 52.1, 74.8, 77.7, 93.3, 104.3, 107.2, 111.2, 116.3, 127.1, 151.7, 156.4, 156.7, 158.1, 161.3, 176.2; MS [M+1]$^+$401.1; Anal. Calcd for $C_{23}H_{28}O_6$: C, 69.0; H, 7.0. Found C, 69.16; H, 7.12; IR (film): 1726, 1605 cm$^{-1}$.

To the methyl ester of 20 obtained above (40 mg, 0.1 mmol) in methanol (2 mL) added KOH (25 mg, 0.45 mmol) in water (1 mL) and stirred at room temperature for 3 h. The reaction mixture was concentrated under vacuum. Water was added to the residue, acidified with 1M HCl and extracted with ethyl acetate. The organic extracts were washed with brine, dried (sodium sulfate) and concentrated under vacuum to obtain 20 ($R_1$=n-propyl, $R_2=R_5=R_6=R_7=H$, $R_3=R_4=R_8=R_9=Me$, Y=OH) (30 mg, 78%) as a white solid. Mp: 140–142° C. $^1H$ NMR (DMSO-d$_6$) δ 0.99 (3H, t, J=7.6 Hz), 1.23 (6H, s), 1.45 (6H, s), 1.59 (2H, m), 2.86 (2H, t, J=8.0 Hz), 4.06 (2H, s), 5.72 (1H, d, J=9.9 Hz), 6.02 (1H, s), 6.50 (1H, d, J=10.2 Hz), 6.63 (1H, s); $^{13}C$-NMR (CDCl$_3$) δ 13.8, 22.1, 23.0, 27.7, 38.3, 43.1, 74.4, 77.7, 93.3, 104.3, 107.3, 111.2, 116.4, 127.1, 151.8, 156.4, 156.6, 158.2, 161.4, 181.4; MS [M+1]$^+$387.2; Anal. Calcd for $C_{22}H_{26}O_6$+0.2 eq $H_2O$: C, 67.75; H, 6.92. Found C, 67.7; H, 6.8; IR (film): 3381, 2750, 1740, 1605 cm$^{-1}$.

EXAMPLE 25

Compound 21 ($R_1$=n-propyl, $R_2=R_5=R_6=R_7=H$, $R_3=R_4=R_8=R_9=Me$)

To acid 20 ($R_1$=n-propyl, $R_2=R_5=R_6=R_7=H$, $R_3=R_4=R_8=R_9=Me$, Y=OH) (120 mg, 0.31 mmol) in benzene (3 mL) added thionyl chloride (90 μL, 1.24 mmol) and refluxed under nitrogen for 1 h. The reaction mixture was cooled to room temperature and concentrated under vacuum. The residue was dissolved in $CH_2Cl_2$ and concentrated under vacuum. This process was repeated twice. The reaction mixture was then dissolved in xylene (3 mL). Nafion NR-50 (50 mg) was added to the reaction mixture and refluxed for 22 h. Cooled to room temperature, filtered the resin, diluted with ethyl acetate and washed with aqueous saturated sodium bicarbonate solution and brine. The organic extracts were dried over sodium sulfate and concentrated under vacuum. The crude product was then purified by preparative TLC (10% ethyl acetate in hexanes) to obtain 21 ($R_1$=n-propyl, $R_2=R_5=R_6=R_7=H$, $R_3=R_4=R_8=R_9=Me$) (15 mg, 13%). $^1H$-NMR (CDCl$_3$) δ 1.03 (3H, t, J=7.4 Hz), 1.21 (6H, s), 1.54 (6H, s), 1.67 (2H, m), 2.88 (2H, t, J=7.6 Hz), 4.21 (2H, s), 5.60 (1H, d, J=9.9 Hz), 6.05 (1H, s), 6.65 (1H, d, J=10.2 Hz); MS [M+1]$^+$369.2.

EXAMPLE 26

Compound 23 ($R_6=R_8=R_9=H$, $R_7=Me$, Z=TBDMS)

To a suspension of sodium hydride (4 g, 0.1 mol) in THF (200 mL) added 1,3-dihydroxybutane (9 mL, 0.1 mol) and stirred at room temperature for 45 min, at which time a large amount of an opaque white precipitate had formed. The tert-butyldimethylsilyl chloride (15.1 g, 0.1 mol) was added and the reaction mixture was allowed to stir at room temperature overnight. The mixture was diluted with ether (500 mL) and washed with 10% aqueous potassium carbonate (150 mL), brine (100 mL). The organic extracts were dried over sodium sulfate and concentrated under vacuum to obtain a colorless oil (20 g). A portion of the crude product (1 g) was purified by silica gel chromatography (8/1 hexane/ethyl acetate) to obtain 23 ($R_6=R_8=R_9=H$, $R_7=Me$, Z=TBDMS) (700 mg) as a colorless oil. $^1H$ NMR (CDCl$_3$) δ 0.08 (6H, s), 0.90 (9H, s), 1.19 (3H, d, J=6.3 Hz), 1.62–1.70 (2H, m), 3.23 (1H, br s), 3.77–3.99 (2H, m), 4.02–4.07 (1H, m); $^{13}C$ NMR (CDCl$_3$) δ −5.7 (2C), 23.2, 25.6, 25.7 (3C), 39.8, 62.7, 68.2; MS [M+1]$^+$204.9.

EXAMPLE 27

Compound 24 ($R_1$=n-propyl, $R_2=R_5=R_6=R_8=R_9=H$, $R_3=R_4=R_7=Me$, Z=TBDMS)

To monophenol 6 (72 mg, 0.25 mmol), triphenylphosphine (98.4 mg, 0.375 mmol) and 23 ($R_6=R_8=R_9=H$, $R_7=Me$, Z=TBDMS) (77 mg, 0.375 mmol) in THF (5 mL) added DEAD (60 μL, 0.375 mmol) and stirred at room temperature under nitrogen for 1.5 h. The reaction mixture was concentrated under vacuum and purified by silica gel chromatography (3/1 hexane/ethyl acetate) to obtain 24 ($R_1$=n-propyl, $R_2=R_5=R_6=R_8=R_9=H$, $R_3=R_4=R_7=Me$, Z=TBDMS) (111 mg, 94%) as an oil. $^1H$ NMR (CDCl$_3$) δ −0.02 (6H, s), 0.89 (9H, s), 1.03 (3H, t, J=7.2 Hz), 1.19 (3H, d, J=6.3 Hz), 1.49 (6H, s), 1.63–1.73 (2H, m), 1.79–2.02 (2H, m), 2.88 (2H, t, J=6.0 Hz), 3.71–3.76 (2H, m), 4.59–4.65 (1H, m), 5.52 (1H, d, J=9.9 Hz), 5.95 (1H, s), 6.44 (1H, s), 6.64 (1H, d, J=9.9 Hz); $^{13}C$-NMR (CDCl$_3$) δ −5.6(2C), 13.8, 18.4, 19.6, 23.1, 25.7 (3C), 27.7, 38.3, 39.4, 59.1, 71.7, 94.2, 103.8, 106.3, 107.8, 110.8, 116.9, 126.7, 151.8, 156.3, 156.5, 158.2, 161.5; Anal. Calcd for $C_{27}H_{40}O_5Si$: C, 68.6; H, 8.53. Found C, 68.9; H, 8.6; IR (film): 2959, 2872, 1736, 1605 cm$^{-1}$; MS [M+1]$^+$473.2.

EXAMPLE 28

Compound 24 ($R_1$=n-propyl, $R=R_2=R_5=R_6=R_8=R_9=H$, $R_3=R_4=R_7=Me$)

To 24 ($R_1$=n-propyl, $R_2=R_5=R_6=R_8=R_9=H$, $R_3=R_4=R_7=Me$, Z=TBDMS) (176 mg, 0.372 mmol) in THF (8 mL)

added TBAF (1.0 M soln in THF, 560 μL) and stirred at room temperature overnight. The reaction mixture was acidified with 1M HCl and extracted with ethyl acetate. The organic extracts were then washed with water, brine, dried (sodium sulfate) and concentrated under vacuum. The crude product was purified by silica gel chromatography (1/1 hexane/ethyl acetate) to obtain 24 ($R^1$=n-propyl, $R=R_2=R_5=R_6=R_8=R_9$=H, $R_3=R_4=R_7$=Me) (133 mg, 100%) as an oil. $^1$H NMR (CDCl$_3$) δ 1.03 (3H, t, J=7.5 Hz), 1.38 (3H, d, J=6.0 Hz), 1.49 (6H, s), 1.65–1.79 (2H, m), 1.94–2.05 (2H, m), 2.88 (2H, t, J=6.0 Hz), 3.81 (2H, t, J=5.7 Hz), 4.65–4.67 (1H, m), 5.52 (1H, d, J=9.9 Hz), 5.95 (1H, s), 6.46 (1H, s), 6.62 (1H, J=10.2 Hz); $^{13}$C-NM(CDl$_3$) δ 13.9, 15.1, 19.7, 23.1, 27.7, 38.3, 38.9, 59.3, 72.4, 77.6, 94.2, 104.1, 107.8, 110.9, 116.7, 126.9, 151.9, 156.0, 156.4, 158.2, 161.4; $C_{21}H_{26}O_5$+0.3 eq $H_2O$: C, 69.32; H, 7.37. Found C, 69.25; H, 7.39; IR (film): 3474, 2971, 1738, 1593 cm$^{-1}$; MS [M+1]$^+$ 359.1.

References

1a. Brookmeyer, R., Reconstruction and Future Trends of the AIDS Epidemic in the United States, *Science*, 1991, 253, 37–42.
b. Brain, M. M.; Heyward, W. L.; Curran, J. W.; The Global Epidemiology of HIV Infection and AIDS, *Annu. Rev. Microbiol.*, 1990, 44, 555–577.
2a. Weislow, O. S.; Kiser, R.; Fine, D. L.: Bader, J. Shoemaker, R. H.; Boyd, M. R., New Soluble-formazan Assay for HIV-1 Cytopathic Effects: Application to High-Flux Screening of Synthetic and Natural Products of AIDS-Antiviral Activity. *J. Natl. Cancer Inst.*, 1989, 81, 577–586.
b. Mitsuya, H.; Yarchoan, R.; Broder, S., Molecular Targets for AIDS Therapy. *Science*, 1990, 249, 1533–1544.
c. Petteway, S. R., Jr.; Lambert, D. M.; Metcalf, B. W., The Chronically Infected Cells: A Target for the Treatment of HIV Infection and AIDS. *Trends Phanmacol. Sci.*, 1991, 12, 28–34.
d. Richman, D. D., Antiviral Therapy of HIV Infection, *Annu. Rev. Med.*, 1991, 42, 69–90.
e. Haden, J. W., Immunotherapy of Human Immnunodeficiency Virus Infection. *Trends Pharmacol Sci.*, 1991, 12, 107–111.
f. Huff, J. R., HIV Protease: A Novel Chemotherapeutic Target for AIDS. *J. Med. Chem.*, 1991, 34, 2305–2314.
g. De Clercq, E., HIV Inhibitors Targeted at the Reverse Transcriptase. *AIDS Research and Human Retroviruses*, 1992, 8, 119–134.
3. Kashman, Y.; Gustafson, K. R.; Fuller, R. W.; Cardellina, J. H., II; McMahon; J. B.; Currens, M. J.; Buckheit, R. W., Jr.; Hughes, S. H.; Cragg, G. M.; Boyd, M. R., The Calanolides, a Novel HIV-Inhibitory Class of Coumarin Derivatives from the Tropical Rainforest Tree, *Calophyllum lanigerum. J. Med. Chem.* 1992, 35, 2735–2743.
4. Hoofnagle, J. H. Chronic hepatitis B, *N. Engl. J Med.* 1990, 323, 337–339.
5. Martin, P. and Friedman, L. S. In *Innovations in Antiviral Development and the Detection of Virus Infections*; T. M. Block; D. Junkind; R. L. Crowell; M. Dension; L. R. Walsh, Ed.; Plenum Press: New York, 1992, 111–120.
6. Aach, R. D. The treatment of chronic type B viral hepatitis. *Ann. Intern. Med.* 1988, 109, 88–91.
7. Alexander, G. J.; Brahm, J.; Fagan, E. A.; Smith, H. M.; Daniels, H. M.; Eddleston, A. L.; Williams, R., Loss of HBSAg with interferon therapy in chronic hepatitis B virus infection. *Lancet* 1987, ii, 66–69.
8. Hoofnagle, J. H.; Di Bisceglie, A. M. Antiviral therapy of viral hepatitis. In *Antiviral Agents and Viral Diseases of Man*; G. J. Galasso; R. J. Whiteley; T. C. Merigan, Ed; Raven Press: New York, 1972, 415–457.
9. Yokosuka, O.; Omata, O. M.; Imazeki, F.; Okauda, K.; Summers, J. Changes of hepatitis B virus DNA in liver and serum caused by recombinant leukocyte interferon treatment: analysis of intrahepatic replicative hepatitis B virus DNA. *Hepatology* 1985, 5, 728–734.
10. Doong, S. L.; Tsai, C. H.; Schinazi, R. F.; Liota, D. C.; Cheng, Y. C. Inhibition of the replication of hepatitis B virus in vitro by 2',3'-dideoxy-3'-thiacytidine and related analogues. *Pro. Natl. Acad. Sci. USA* 1991, 88, 8495–99.
11. Schlam, S. W.; de Man, R. A.; Heijtink, R. A.; Niesters, G. M. New nucleoside analogues for chronic hepatitis B. *J. Hepatalogy* 1995, 22, 52–56.
12. van Leeuwen R.; Katlama, C.; Kitchen, V.; Boucher, C. A. B.; Tubiana, R.; McBride, M.; Ingrand, D.; Weber, J.; Hill, A.; McDade, H.; Danner, S. A. Evaluation of safety and efficacy of 3TC (Lamivudine) in patients with asymptomatic or mildly symptomatic human immunodeficiency virus infection: A phase I/II study. *J. Inf. Dis.* 1995, 171, 1166–71.
13. Kaplan, M. M.; Webster, R. G. The epidemiology of influenza, *Sci. Am.*, 1977, 236 (6), 88–105.
14. Hoffman, C. E. Amantadine HCl and related compounds. In *Selective Inhibitors of Viral Functions*; Carter, W. A., Ed.; CRC Press: Cleveland, 1973, 199.
15. Dolin, R.; Reichman, R. C.; Madore, H. P.; Maynard, R.; Lindon, P. M.; Webber-Jones, J. A controlled trial of amantadine and rimandatine in the prophylaxis of influenza A infections. *N. Engl. J. Med.* 1982, 307, 580–584.
16. Oxford, J. S.; Galbraith, A. Anti-influenza virus activity of amantadine: A selective review of laboratory and clinical data: In *Viral Chemotherapy*; Shugar D. Ed.; Pergamon Press, 1985, 169–254.
17. Couch, R. B.; Jackson, G. G. Antiviral agents in influenza—Summary of influenza workshop VIII. *J. Infect. Dis.* 1976, 134, 516–527.
18. Bryson, Y. J.; Monahan, C.; Pollack, M.; Shields, W. D. A prospective double-blind study of side effects associated with the administration of amantadine for influenza A virus prophylaxis. *J. Infect. Dis.* 1980, 141, 543–547.
19. Tsunoda, A.; Maasab, H. H.; Cochran, K. W.; Eveland, W. C. Antiviral activity of α-methyl-1-adamantane methylamnine hydrochloride. *Antimicrob. Agents Chemother.* 1966, 553.
20. Tisdale, M.; Bauer, D. J. The relative potencies of anti-influenza compounds. *Ann. N.Y. Acad. Sci.* 1977, 284, 254–263.
21. Degelau, J; Somani, S. K.; Cooper, S. L.; Guay, D. R. P.; Crossley, K. B. Amantadine-resistant influenza A in a nursing facility. *Arch. Intern. Med.* 1992, 152, 390–392.
22. Hayden, F. G.; Belshe, R. B.; Clover, R. D.; Hay, A. J.; Oakers, M. G.; Soo, W. Emergence and apparent transmission of rimantadine-resistant influenza virus in families. *N. Engl. J. Med.* 1989, 321, 1696–1702.
23. Mast, E. E.; Harmon, M. W.; Gravenstein, S.; Wu, S. P.; Arden, H. H.; Circo, R.; Tyszka, G.; Kendal, A. P.; Davis, J. P. Emergence and possible transmission of arnantadine-resistant viruses during nursing home outbreaks of influenza A (H3N2). *Am J. Epidemiol.* 1992, 134, 988–997.
24. Hayden, F. G.; Couch, R. B. Clinical and epidemiological importance of influenza A viruses resistant to arnantadine and rimantadine. *Rev. Med. Virol.*, 1992, 2, 89–96.
25. Kimberlin, D. W.; Crampacker, C. S.; Straus, S. E.; Biron, K. K.; Drew, W. L.; Hayden, F. G.; McKinlay, M.; Richman, D. D.; Whitley, R. J. Antiviral resistance in clinical practice. *Antiviral Res.*, 1995, 26, 423–438.

26. Knight, V.; Gilbert, B. E. Ribavirin aerosol treatment of influenza. In *Infectious Disease Clinics of North America*, Vol 1.; Moellering, Jr.. Ed.; 1987, 441–57.
27. Ray, C. G.; Icenogle, T. B.; Minnich, L. L; Copeland, J. G.; Grogan, T. M. The use of intravenous ribavirin to treat influenza virus-associated acute myocarditis. *J. Infect Dis.*, 1989, 159, 829–836.
28. Hoover, D. R.; Saah, A. J.; Bacellar, H.; Phair, J.; Detels, R.; Anderson, R.; Kaslow, R. A. Clinical manifestations of AIDS in the Era of *Pneumocysis* Prophylaxis. *N. Eng. J. Med.* 1993, 329, 1922–1926.
29. Studies of the Ocular Complications of AIDS Research Group, AIDS clinical Trials Group. Mortality in Patients with the Acquired Immunodeficiency Syndrome Treated with Either Foscarnet or Ganciclovir for Cytomegaloviruse Retinitis. *N. Eng. J. Med.* 1992, 326, 213–220.
30. Gelb, C. D. In *The Human Herpesviruses*, New York, 1993, 288–300.
31. Dellamonica, P. et al. *Clin. Pharmacol.* 1991, 10, 301.
32. Smith, J. Strategies against Herpes Simplex Virus. *Intl. Antiviral News* 1997, 5, 223–225.
33. Patil, A. D.; Freyer, A. J.; Eggleston, D. S.; Haltiwanger, R. C.; Bean, M.. F.; Taylor, P. B.; Caranfa, M. J.; Breen, A. L.; Bartus, H. R.; Johnson, R. K.; Hertzberg, R. P.; Westley, J. W. The Inophyllums, Novel Inhibitors of HIV-1 Reverse Transcriptase Isolated from the Malaysian Tree, *Calophyllum inophyllum* Linn. *J. Med. Chem.* 1993, 36, 4131–4138.
34. Fuller, R. W.; Bokesch, H. R.; Gustafson, K. R.; McKee, T. C.; Cardellina, J. H, II; McMahon, J. B.; Cragg, G. M.; Soejarto, D. D.; Boyd, M. R. HIV-Inhibitory Coumarins from Latex of the Tropical Rainforest Tree *Calophyllum teysmannii* var. *inophylloide*. *Bioorg. & Med. Chem. Lett.* 1994, 4, 1961–1964.
35. Gustafson, K. R.; Bokesch, H. R.; Fuller, R. W.; Cardellina, J. H, II; Kadushin, M. R.; Soejarto, D. D.; Boyd, M. R. Calanone, a Novel Coumarin from *Calophyllum teysmannii*. *Tetrahedron Lett.* 1994, 35, 5821–5824.
36. Dharmaratne, H. R. W.; Wanigasekera, W. M. A. P.; Mata-Greenwood, E.; Pezzuto, J. M. Inhibition of Human Immunodeficiency Virus Type 1 Reverse Transcriptase Activity by Cordatolides Isolated from *Calophyllum cordato-oblongum*. *Planta Med.* 1998, 64, 460–461.
37. McKee, T. C.; Convington, C. D.; Fuller, R. W.; Bokesch, H. R.; Young, S.; Cardellina, J. H., II; Kadushin, M. R.; Soejarto, D. D.; Stevens, P. F.; Cragg, G. M.; Boyd, M. R. Pyranocoumarins from Tropical Species of the Genus *Calophyllum*: A Chemotaxonomic Study of Extracts in the National Cancer Institute Collection. *J. Nat. Prod.* 1998, 61, 1252–1256.
38. Spino, C.; Dodier, M.; Sotheeswaran, S. Anti-HIV Coumarins from Calophyllum Seed Oil. *Bioorg. Med. Chem. Lett.* 1998, 8, 3475–3478.
39. Galinis, D. L.; Fuller, R. W.; McKee, T. C.; Cardellina, J. H, II; Gulakowski, R. J.; McMahon, J. B.; Boyd, M. R. Structure-Activity Modifications of the HIV-1 Inhibitors (+)-Calanolide A and (−)-Calanolide B. *J. Med. Chem.* 1996, 39, 4507–4510.
40. Zhou, C. M.; Wang, L.; Zhao, Z. Z. Synthesis of 11-Demehtyl and 6,6,11-Demehtyl Calanolide A. *Chinese Chem. Lett.* 1997, 8, 859–860.
41. David E. Zembower, Shuyuan Liao, Michael T. Flavin, Ze-Qi Xu, Tracy L. Stup, Robert W. Buckheit, Jr., Albert Khilevich, Aye Aye Mar and Abram K. Sheinkman, Structural Analogues of the Calanolide Anti-HIV Agents. Modification of the trans-10,11-Dimethyldihydropyran-12-ol Ring (Ring C). *J. Med. Chem.* 1997, 40, 1005–1017.
42. Frank, P.; Flavin, M. T.; Roca-Acin, J.; Xu, Z.-Q. Safety Assessment of (+)-Calanolide A, A Naturally Occurring Anti-HIV Agent. *4th Conference on Retroviruses ans Opportunistic Infections*, Jan. 22–26, 1997, Washington, D.C., Abstract No. 225.
43. Jon Ruckle, Jeremey Giltner, Terri Creagh, Bipul Dutta, Dwain Tolbert and Ze-Qi Xu, Clinical Safety and Pharmacokinetics of (+)-Calanolide A, A Naturally Occurring NNRTI in Normal Healthy and HIV-Infected Volunteers. *5th Conference on Retroviruses and Opportunistic Infections*, Jan. 31–Feb. 4, 1999, Chicago, Ill., Abstract No. 606.
44. Kucherenko, A.; Flavin, M. T.; Boulanger, W. A.; Khilevich, A.; Shone, R. L.; Rizzo, J. D.; Sheinkinan, A. K.; Xu, Z.-Q. Novel Approach for Synthesis of (±)-Calanolide A and Its Anti-HIV Activity. *Tetrahedron Lett.* 1995, 36, 5475–5478.
45. Flavin, M. T.; Rizzo, J. D.; Khilevich, A.; Kucherenko, A.; Sheinkman, A. K.; Vilaychack, V.; Lin, L.; Chen, W.; Greenwood, E. M.; Pengsuparp, T.; Pezzuto, J. M.; Hughes, S. H.; Flavin, T. M.; Cibulski, M.; Boulanger, W. A.; Shone, R. L.; Xu, Z.-Q. Synthesis, Chromatographic Resolution and Anti-HIV Activity of (±)-Calanolide A and Its Enantiomers. *J. Med. Chem.* 1996, 39, 1303–1313.
46. Khilevich, A.; Mar, A.; Flavin, M. T.; Rizzo, J. D.; Dzekhtser, S.; Brankovic, D.; Lin, L.; Zhang, H.; Chen, W.; Liao, S.; Zembower, D. E.; Xu, Z.-Q. Synthesis of (+)-Calanolide A, An Anti-HIV Agent, via Enzyme-Catalyzed Resolution of the Aldol Products. *Tetrahedron: Asymmetry* 1996, 7, 3315–3326.
47. Chenera, B.; West, M. L.; Finkelstein, J. A.; Dreyer, G. B. Total Synthesis of (±)-Calanolide A, a Non-nucleoside Inhibitor of HIV-I Reverse Transcriptase. *J. Org. Chem.* 1993, 58, 5605–5606.
48. Palmer, C. J.; Josephs, J. L. Synthesis of the *Calophyllum* coumarins. *Tetrahedron Lett.* 1994, 35, 5363–53166; *J. Chem. Soc. Perkin Trans.* 1, 1995, 3135–3152.
49. Deshapande, P. P.; Tagliaferri. F.; Victory. S. F.; Yan, S.; Baker, D. C. Synthesis of Optically Active Calanolide A and B. *J. Org. Chem.* 1995, 60, 2964–2965.
50. Rehder, K. S.; Kepler, J. A. Total Synthesis of (±)-Calanolide A. *Synthetic Commun.* 1996, 20, 4005–4021.
51. Trost, B. M.; Toste, F. D. A Catalytic Enantioselective Approach to Chromans and Chromanols. A Total Synthesis of (−)-Calanolide A and B and the Vitamin E Nucleus. *J. Am. Chem. Soc.* 1998, 120, 9074–9075.
52. Martin R. Uses of the Fries Rearrangement for the Preparation of Hydroxyarylketones. A Review. *Org. Prep. Proc. Intl.* 1992, 24, 369–435.
53. Desai, B. M.; Desai, P. R. Coumarins from 5-n-Pentadecylresorcinol and the Fries Reaction of Their Esters. *J. Indian Chem. Soc.* 1960, 37, 550–552.
54. Ahluwalia, V. K.; Kumar, D.; Sunita. Studies in 4-Pheylcoumarins: Some Unusual Observations. *Indian J. Chem.* 1975, 13, 546–548.
55. Bell, D.; Davies, M. R.; Geen, G. R.; Mann, I. S. Copper(I) Iodide: A Catalyst for the Improved Synthesis of Aryl Propargyl Ethers. *Synthesis* 1995, 707–712.
56. Games, D. E.; Haskins, N. J. Synthesis of Some Dimethylpyrano- and 3-Methylbut-2-enyl-4-phenyl- and -4-n-propylocoumarins. *J. Chem. Soc., Chem. Commun.*, 1971, 1005–1006.
57. Petit, Y.; Sanner, C.; Larcheveque, M. *Synthesis* 1998, 538
58. Frater, G.; Muller, U.; Gunther, W. *Tetrahedron* 1984, 40, 1269.
59. Kikukawa, T.; hnaida, M.; Tai, A. *Bull. Chem. Soc. Jpn.* 1984, 57, 1954.

60. Nerz-Stormes, M.; Thornton, E. R. *J. Org. Chem.* 1991, 56, 2489.

What we claim:

1. A method for preparing a calanolide analogue having the structure 22:

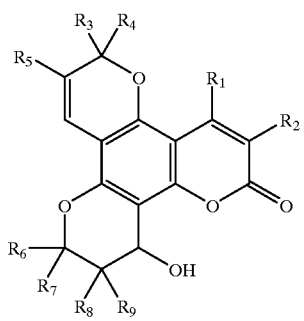

wherein $R_1$ is H, halogen, hydroxyl, amino, $C_{1-6}$ alkyl, aryl-$C_{1-6}$ alkyl, mono- or poly-fluorinated $C_{1-6}$ alkyl, hydroxyl-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl) amino-$C_{1-8}$ alkyl, cyclohexyl, aryl, or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-6}$ alkyl-amino-$C_{1-8}$ alkyl, nitro, azido or halogen;

$R_2$ is H, halogen, hydroxyl, $C_{1-6}$ alkyl, aryl-$C_{1-6}$ alkyl, mono- or poly-fluorinated $C_{1-6}$ alkyl, aryl or heterocycle;

$R_3$ and $R_4$ are independently selected from the group consisting of H, $C_{1-6}$ alkyl, aryl-$C_{1-6}$ alkyl, mono- or poly-fluorinated $C_{1-6}$ alkyl, aryl or heterocycle; or $R_3$ and $R_4$ together form a 5–7 membered saturated cycle ring or heterocycle ring;

$R_5$ is H, halogen, methyl, ethyl;

$R_6$, $R_7$, $R_8$ and $R_9$ are independently selected from the group consisting of H, halogen, hydroxy, amino, mono- or dialkylamino-$C_{1-6}$ alkyl, hydroxy-$C_{1-6}$ alkyl, amino-$C_{1-6}$ alkyl, aryl-$C_{1-6}$ alkyl, mono- or poly-fluorinated $C_{1-6}$ alkyl, aryl or heterocycle; or $R_6$ and $R_7$ together form a 5–7 membered saturated cycle ring or heterocycle ring; or $R_8$ and $R_9$ together form a 5–7 membered saturated cycle ring or heterocycle ring;

said method comprising the steps of:

(a) coupling 1,3,5-trihydroxybenzene with -ketoester 25:

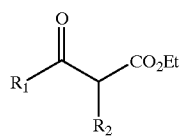

to produce compound 15:

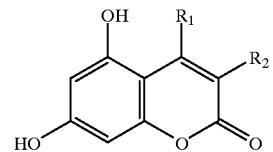

wherein $R_1$ and $R_2$ are the same as described above;

(b) acylating compound 15 with $(RCO)_2O$ wherein R represents $C_{1-6}$ alkyl, aryl-$C_{1-6}$ alkyl, mono- or poly-fluorinated $C_{1-6}$ alkyl, aryl or heterocycle to produce compound 16

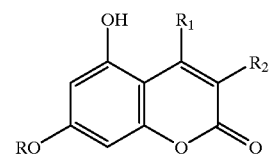

wherein R, $R_1$ and $R_2$ are the same as described above;

(c) coupling compound 16 with compound 26

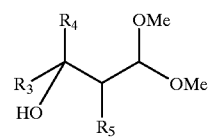

to provide compound 17

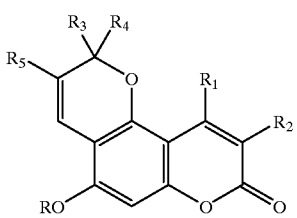

wherein R, $R_1$, $R_2$, $R_3$, $R_4$, and $R_5$ are the same as described above;

(d) hydrolyzing compound 17 to produce compound 18

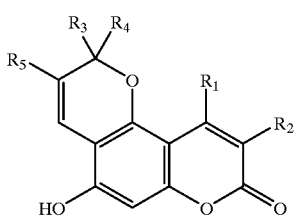

wherein $R_1$, $R_2$, $R_3$, $R_4$, and $R_5$ are the same as described above;

(e) coupling compound 18 with compound 19

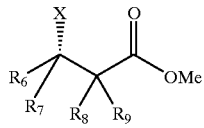

to produce compound 20

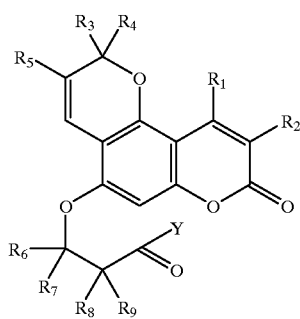

wherein $R_1$, $R_2$, $R_3$, $R_4$, $R_5$, $R_6$, $R_7$, $R_8$, and $R_9$ are the same as described above, Y=OH OMe, X is OH or OTs;

(f) hydrolyzing compound 20 (Y=OMe) to form 20 (Y=OH)

(g) cyclizing compound 20 (Y=OH) in the presence of a Lewis acid to produce compound 21

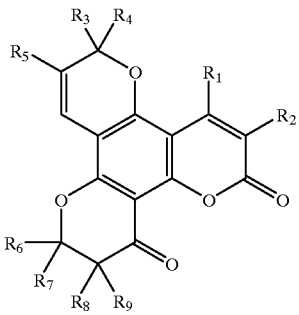

wherein $R_1$, $R_2$, $R_3$, $R_4$, $R_5$, $R_6$, $R_7$, $R_8$, and $R_9$ are the same as described above; and (h) reducing compound 21 to produce compound 22.

2. The method according to claim 1, wherein step (a) coupling is performed in the presence of an acid catalyst.

3. The method according to claim 1, wherein step (b) acylation is performed in the presence of a Lewis acid.

4. The method according to claim 1, wherein step (c) coupling is performed in the presence of a base.

5. The method according to claim 1, wherein step (d) hydrolysis is performed in the presence of a base in aqueous solution.

6. The method according to claim 1, wherein step (e) coupling is performed using triphenylphosphine and diethyl azodicarboxylate.

7. The method according to claim 1, wherein the Lewis acid of step (g) is $AlCl_3$, $TiCl_4$ or $BF_3$.

8. The method according to claim 1, wherein step (h) reduction is performed in the presence of sodium borohydride and cerium chloride.

* * * * *